(12) United States Patent
Barbalatt

(10) Patent No.: US 11,357,791 B2
(45) Date of Patent: Jun. 14, 2022

(54) COMPOSITIONS AND METHODS FOR THE TREATMENT OF SINUS DISEASE AND DISORDERS

(71) Applicant: ENT TECHNOLOGIES PTY LTD, Victoria (AU)

(72) Inventor: Sam Barbalatt, Caulfield North (AU)

(73) Assignee: ENT TECHNOLOGIES PTY LTD, Hawthorn (AU)

( * ) Notice: Subject to any disclaimer, the term of this patent is extended or adjusted under 35 U.S.C. 154(b) by 464 days.

(21) Appl. No.: 15/998,565

(22) PCT Filed: Feb. 17, 2017

(86) PCT No.: PCT/AU2017/050144
§ 371 (c)(1),
(2) Date: Aug. 15, 2018

(87) PCT Pub. No.: WO2017/139854
PCT Pub. Date: Aug. 24, 2017

(65) Prior Publication Data
US 2020/0276226 A1 Sep. 3, 2020

(30) Foreign Application Priority Data
Feb. 17, 2016 (AU) .................................. 2016900553

(51) Int. Cl.
*A61K 31/731* (2006.01)
*A61P 11/00* (2006.01)
*A61K 47/02* (2006.01)

(52) U.S. Cl.
CPC ............ *A61K 31/731* (2013.01); *A61K 47/02* (2013.01); *A61P 11/00* (2018.01)

(58) Field of Classification Search
CPC ........ A61K 31/731; A61K 47/02; A61P 11/00
See application file for complete search history.

(56) References Cited

U.S. PATENT DOCUMENTS 6,214,376 B1 * 4/2001 Gennadios ........... A61K 9/4816
424/451

FOREIGN PATENT DOCUMENTS

| EP | 1930015 A1 | 6/2008 |
|---|---|---|
| WO | 2009/002727 A1 | 12/2008 |
| WO | 2012/103575 A1 | 8/2012 |
| WO | 2012/126777 A1 | 9/2012 |
| WO | 2014/123880 A1 | 8/2014 |
| WO | 2015/082356 A1 | 6/2015 |
| WO | 2017/000935 A1 | 1/2017 |
| WO | 2017/139854 A1 | 8/2017 |

OTHER PUBLICATIONS

Mangione; Biophysical Chemistry; 113 (2005), 129-135.*
Fulcher et al., "Well-Differentiated Human Airway Epithelial Cell Cultures," Human Cell Culture Protocols Springer pp. 183-206 (2005).
Lee et al., "Air-Liquid Interface Culture of Serially Passaged Human Nasal Epithelial Cell Monolayer for In Vitro Drug Transport Studies," Drug Delivery 12(5):305-311 (2005).
Liu et al., "Review for carrageenan-based pharmaceutical biomaterials: Favourable physical features versus adverse biological effects," Carbohydrate Polymers 12(1): 27-36 (2015).
Malik et al., "*Staphyloccus aurenus* impairs the airway epithelial barrier in vitro," Int. Forum Allergy Rhinol. 5(6):551-556 (2015).
Mallants et al., "An improved primary human nasal cell culture for the simultaneous determination of transepithelial transport and ciliary beat frequency," J. Pharm. Pharmacol. 61(7):883-890 (2009).
Murphy et al., "Biofilm quantification on nasolacrimal silastic stents after dacryocystorhinostomy," Ophthal Plast Reconstr Surg. 31(5):396-400 (2015).
Ramezanpour et al., "Th17 Cytokines Disrupt the Airway Mucosal Barrier in Chronic Rhinosinusitis," Mediators of inflammation Volume 2016.
Sisson et al., "All-digital image capture and whole-field analysis of ciliary beat frequency," 211(2):103-111 (2003).
Wang et al., "Preparation and anti-influenza A virus activity of κ-carrageenan oligosaccharide and its sulphated derivatives," Food Chemistry 133:880-888 (2012).
Yamada et al., "Carrageenans can regulate the pulmonary absorption of antiasthmatic drugs and their retention in the rat lung tissues without any membrane damage," International Journal of Pharmaceuticals, 293(2.2):63-72 (2005).
International Search Report issued in International Application No. PCT/AU2017/050144, dated Mar. 20, 2017.
International Preliminary Report on Patentability issued in International Application No. PCT/AU2017/050144, dated Apr. 27, 2018.

* cited by examiner

*Primary Examiner* — Pancham Bakshi
(74) *Attorney, Agent, or Firm* — Medler, Ferro, Woodhouse & Mills PLLC

(57) ABSTRACT

A composition comprising kappa-carrageenan and a carrier solution, wherein the carrier solution is an isotonic solution, and methods of use thereof in the treatment of diseases or conditions of the upper airways.

6 Claims, 28 Drawing Sheets

COMPOSITIONS AND METHODS FOR THE TREATMENT OF SINUS DISEASE AND DISORDERS

TECHNICAL FIELD

Compositions comprising kappa carrageenan for nasal and sinus use, and methods of use thereof.

BACKGROUND ART

The following discussion of the background art is intended to facilitate an understanding of the present invention only. The discussion is not an acknowledgement or admission that any of the material referred to is or was part of the common general knowledge as at the priority date of the application.

The carrageenans are a group of naturally occurring linear sulfated galactose-based polysaccharides derived from specific types of red seaweeds. The traditional use of carrageenans was as gelling agents in food products. However, more recently carrageenans have been tested for use in the pharmaceutical industry, showing an association with improved drug formulations, such as sustained release formulations, and in the production of biomaterials. However, they have also been associated with adverse responses such as inhibition of blood coagulation and adverse effects on the immune system. Therefore, there are some risks associated with the use of carrageenans in the pharmaceutical industry which has limited their use in pharmaceutical compositions and preparations.

Although there are at least ten different types of carrageenan known to be extracted from seaweed, there are three main types which have been used in industry, including iota-, kappa- and lambda-carrageenan. These carrageenans are different from each other in both their structure and the number of sulfate groups.

Food grade carrageenans have been used for a long time. Since the carrageenans have a gelling property when placed in contact with potassium and calcium ions, they have been used in many food products to improve consistency of the product. The carrageenans are not significantly absorbed from the gastrointestinal tract following oral administration and as such are generally considered safe. However, recent studies have shown that the use of carrageenans in pharmaceuticals and biomaterials, such as drug delivery systems or tissue regeneration scaffolds may result in adverse activities towards the immune system and blood coagulation. A recent review article provides a discussion on the adverse biological effects of carrageenans (Liu et al., (2015) Carbohydrate Polymers 121: 27-36).

Iota-carrageenan has recently been considered for use as an antiviral agent to treat rhinovirus infections. However, very little is known about the use of kappa-carrageenan either alone or in combination with other carrageenans.

Products, such as nasal sprays or drops for the treatment of upper airway diseases are often ineffective in treating sinus pathologies as the dose delivered by these devices is insufficient to reach the area to be treated. A further problem that is encountered with treating sinus disease is that the medication is not in contact with the area for a sufficient period of time to be therapeutically effective.

There are a number of diseases and conditions of the upper airways, including rhinitis, allergic rhinitis, non-allergic rhinitis, sinusitis, rhinosinusitis and chronic rhinosinusitis. Chronic Rhinosinusitis (CRS) is characterised by an immune disorder resulting in chronic inflammation affecting the nose and paranasal sinuses. This pathology manifests symptomatically as nasal obstruction, production of copious amounts of thick green mucus, sinus pain, headache, loss of sense of smell, sore throat and cough.

There are several phenotypes of chronic rhinosinusitis and each has a preferred treatment protocol. In any event all phenotypes require daily nasal and sinus irrigation with large volume positive pressure solutions to remove excess mucus and inflammatory mediators from the nasal and sinus cavities to relieve symptoms. Some forms of the disease require the administration of topical medication mixed into the irrigation solutions. Such topical therapies include topical steroids like budesonide, or mometasone and/or topical antibiotics.

CRS is also characterised by histological abnormalities whereby the function and structure of mucosal cilia are adversely affected. This results in mucus stagnation whereby it becomes thick and concentrated resulting in an increased incidence of infection. There is also "leaking" of the mucosa whereby the inflammatory changes adversely affect the integrity of the mucous membrane and bacteria, and inflammatory materials can traverse into the submucosa.

The problem with delivering topical therapies in the abovementioned manner is that the concentration of medicament that remains in the paranasal sinuses after irrigation is extremely low. This occurs because 97.5% of the irrigation solution used is lost after treatment. Hence only 2.5% remains behind and this quantity of fluid can only contain minute amounts of the topical treatment medication.

It is against this background that the present invention has been developed. The present invention seeks to overcome, or at least ameliorate, one or more of the deficiencies of the prior art mentioned above, or to provide the consumer with a useful or commercial choice.

SUMMARY OF INVENTION

The present invention relates to compositions comprising a therapeutically effective amount of carrageenan in a sinus irrigation solution, and methods of use thereof. More specifically, the carrageenan is kappa-carrageenan.

In one aspect of the present invention there is provided a composition comprising kappa-carrageenan in a carrier solution, wherein the carrier solution is isotonic solution, with extracellular fluids.

In an embodiment of the present invention, the carrier solution comprises NaCl and KCl. The carrier solution may also comprise one or more of the following components: calcium lactate pentahydrate, sodium bicarbonate, glucose, xylitol, or any other five (5) carbon sugar molecule (sugar alcohol), including erythritol and other polyol-sugars. The carrier solution may also have a low ionic strength.

In a second aspect of the present invention there is provided a composition comprising kappa-carrageenan in an isotonic carrier solution, further comprising a second active agent. The second active agent may be in the form of a medicament, medication or agent that is used in the treatment of a disease or condition of the upper airways.

In a third aspect of the present invention there is provided a method for the treatment of a disease or condition of the upper airways, the method comprising administering to a patient in need thereof a composition comprising a therapeutically effective amount of kappa-carrageenan in an isotonic carrier solution.

In a fourth aspect of the present invention, there is provided a kit comprising: a therapeutic amount of kappa-carrageenan in a powdered form, powders to be reconstituted to prepare the carrier solution, and instructions for their use. The kit of the present invention may also include a positive pressure irrigation device or other device which administers the solution to achieve the same or similar therapeutic effect.

In a fifth aspect of the present invention, there is provided the use of kappa-carrageenan in the preparation of a medicament for the treatment of a disease or condition of the upper airways.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which.

DESCRIPTION OF EMBODIMENTS

General Description of the Invention

Figure 1A:
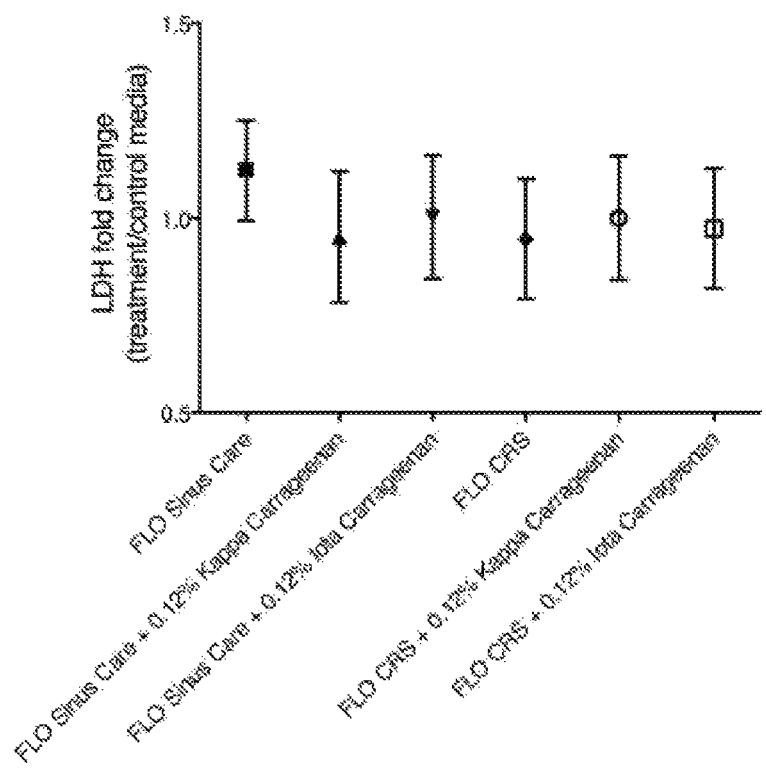
FIG. 1A is a graph showing lactate dehydrogenase expression in the supernatant of human nasal epithelial cells exposed to 24 hours of carrageenan in FLO Sinus Care or FLO CRS solution. Expressed as fold change compared to control media (control media=1); error bars represent standard deviation.

Throughout this specification, unless the context requires otherwise, the word "comprise" or variations such as "comprises" or "comprising", will be understood to imply the inclusion of a stated integer or group of integers but not the exclusion of any other integer or group of integers.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg. size, displacement and field strength etc). A range of values will be understood to include all values within the range, including the values defining the range, and values adjacent to the range which lead to the same or substantially the same outcome as the values immediately adjacent to that value which defines the boundary to the range.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs. The term "active agent" may mean one active agent, or may encompass two or more active agents.

The term "active agent" refers to a compound useful for effecting some beneficial change in the subject to which it is administered. For example, "active agents" within the scope of this definition include kappa carrageenan, steroids, antibiotics, anti-viral agents, antibiotics, antifungal agents and anti-inflammatory agents.

The term "effective amount" or "therapeutic amount" refers to that amount which is sufficient to effect the desired change in the subject. It is within the knowledge and skill of a person skilled in the art to determine the effective amount of an active agent.

The term "treatment" as used herein covers any treatment of a disease in an animal (including a human being) and includes: (i) preventing the disease from occurring' (ii) inhibiting the disease, such as arresting its development; (iii) relieve the disease, for example, causing regression of the disease; and/or (iv) modifying normal biological activity.

The term "diseases", "disorders" or "conditions" as used herein covers any medical diseases/disorders/conditions such as but not limited to Chronic Rhinosinusitis and other diseases which can lead to excessive mucus build up in the nasal passages and paranasal sinus cavities. Additional diseases/disorders/conditions include non-allergic paranasal sinus disease, asthma, allergic rhinitis, Chronic Obstructive Pulmonary Disease, and Cystic Fibrosis. Mucus build up in the nasal passages and paranasal sinus cavities may also result from surgery such as endoscopic sinus surgery.

The term "isotonic" refers to a carrier solution which is isotonic with extracellular fluids.

Any solution that contains one or more salts has an ionic strength or electric charge. The amount of a salt or different salts in solution can be defined by its concentration (mM or mMol). For example, a 10 mM sodium phosphate buffer solution has an ionic strength of 21 mM. Normal saline has a concentration of 9 g/L of sodium chloride and an ionic strength of 154 mM. Commercially available irrigation solutions are often composed of a number of different salts, and have been estimated to have an ionic strength ranging from 130 mM to greater than 500 mM. An ionic strength between 0 to 35 mM is considered to be ultra or very low ionic strength solution when used as a delivery solution. A very low ionic strength means a solution having an ionic strength of less than about 31 mM.

The pharmaceutical preparation of the present invention may be administered to any mammal. Preferably, the mammal is a human being.

DETAILED DESCRIPTION OF THE INVENTION

The compositions and methods of the present invention are useful for the treatment of the upper airways, including the nostrils, nasal cavity and the paranasal sinuses. The paranasal sinuses are joined to the nasal cavity via ostia. As a result of post-operative surgery, complications, infection or disease, the paranasal sinuses, nasal cavity and ostia may become blocked. A person skilled in the art would be aware of other diseases and conditions associated with the upper airways which may be treated by the compositions of the present invention.

The compositions of the prevent invention comprise kappa-carrageenan in an isotonic carrier solution. The composition is preferably administered in a large (e.g. 100-200 ml) volume of carrier solution. Additional medicaments, medications or active agents may also be included in the kappa-carrageenan composition to assist in the treatment of a disease or condition associated with the upper airways.

Kappa-Carrageenan

To date, it is believed that kappa-carrageenan has not been used in pharmaceutical preparations alone without the presence of other carrageenans. That is, although both iota and/or lambda have been the subject of studies for their effects as in delivering active agents in the pharmaceutical industry, there are no corresponding studies for kappa-carrageenan used without one of the other carrageenans present.

Kappa-carrageenan may be obtained from any commercial source. For example natural grade or filtered carrageenan may be obtained from suppliers. The kappa-carrageenan may be in the form of a powder, gel or liquid. Preferably the kappa-carrageenan is in the powdered form.

Studies have shown that iota carrageenan can induce bleeding and lambda carrageenan is very much pro-inflammatory and is used in pain model experiments to induce severe pain. On the other hand, Kappa-carrageenan is the only one of these three carrageenans which has no negative effect and which may offer significant advantages in the delivery of topical medications.

Without being bound by theory, the benefit of using kappa-carrageenan is due, at least in part to its strong mucoadhesive property. The use of kappa-carrageenan with isotonic carrier solutions has been shown not to be pro-inflammatory and very safe when used on nasal and sinus mucosa. In addition, the compositions of the present invention may assist in retaining a medicament or medication on the mucosal surface for significantly longer periods of time than would be the case when simple saline solutions are used to carry the medicament/medication.

Without being bound by theory, the applicant believes that the use of kappa-carrageenan in the sinus solutions of the present invention results in the hydration of the mucus layers with improved innate immune function and cilia motility. In addition, since the irrigation solutions and topical medicaments are retained on the mucosal layers, there is an improved clinical outcome for the treatment regimes.

Furthermore, kappa-carrageenan is hygroscopic and retains water very effectively. Thus, the compositions of the present invention are ideal for treating diseases or conditions of the upper airways.

A therapeutically effective amount of kappa-carrageenan is provided in a carrier solution. The amount of kappa-carrageenan present in the carrier solution ranges from between about 0.01% wt/v to about 15% wt/v, and more preferably between about 0.05% wt/v and about 0.5% wt/v. In one embodiment of the present invention, the amount of kappa-carrageenan present in the carrier solution is about 0.12% wt/v.

The kappa-carrageenan may be provided as a powder or as a liquid solution which is added to the carrier solution. In one embodiment, an amount of kappa-carrageenan is provided to be added to a powdered form of the carrier solution. The carrier solution may be prepared from a powder in accordance with instructions, and then prior to use the kappa-carrageenan may be added. Alternatively, the kappa-carrageenan is provided in a powder form together with the powdered form of the carrier solution, and is made up to the appropriate volume with water.

Thus, in one highly preferred embodiment, the present invention provides compositions comprising kappa-carrageenan in a sinus irrigating solution for the management of patients in the immediate postoperative phase of sinus surgery (sinus irrigation) as well as ongoing sinus irrigation treatment of all inflammatory diseases of the paranasal sinuses where the treatment comprises either simple irrigation or inclusion of therapeutic agents to manage inflammation or infection of the paranasal sinuses.

The composition of the present invention is useful for nasal and sinus use in the presence of any inflammatory condition with or without secondary infection of the upper airways.

In addition, the composition of the present invention may be used in association with other topical therapeutic agents, medicaments or medications, such as but not limited to antibiotics, antifungal agents, or anti-inflammatory agents.

In a preferred embodiment of the invention, the kappa carrageenan is delivered in a volume of between 100 to 200 ml of sinus solution. Preferably, the sinus solution is a low ionic strength solution. The sinus solution may also contain xylitol, or erythritol (or any other 5 carbon sugar or polyol) and some low concentrations of both KCl and NaCl.

Carrier Solutions

The compositions of the present invention may be prepared by combining a therapeutically effective amount of kappa-carrageenan in an isotonic carrier solution (also referred to as "isotonic solution"). The sinus solutions appropriate for use with kappa-carrageenan include any diluent or carrier which is known to the person skilled in the art. Although any isotonic carrier solution may be used in combination with the kappa-carrageenan, the best results are achieved with an isotonic solution comprising NaCl and KCl.

Preferably, isotonic solutions that may be used in combination with kappa-carrageenan are commercially available, including FLO® Sinus Care and FLO® CRS solution. FLO® Sinus Care is an isotonic solution, comprising NaCl, KCL, calcium lactate pentahydrate, sodium bicarbonate and glucose. The solution may be provided as a powder and made up to volume in accordance with manufacturer's instructions and then combined with a therapeutic amount of kappa-carrageenan. Alternatively, kappa-carrageenan may be added to the powdered form of the carrier solution, and made up to the required volume, to ensure delivery of a therapeutic amount of the kappa-carrageenan.

In a preferred embodiment, a powdered form of the kappa-carrageenan is combined with the powder of the isotonic carrier and then made up to the required volume with water. The combined components may be prepared and packaged in a powdered form.

In some circumstances, a low ionic strength solution is preferable, for example patients with Chronic Rhinosinusitis, as low ionic strength solutions do not adversely affect the innate immune function in these patients. In this instance, it is preferable to use FLO® CRS solution, which has a low ionic strength, and comprises xylitol, KCl, and NaCl.

Preferably, the FLO Sinus Care has the following composition: 0.772% w/v NaCl, 0.042% w/v KCl, 0.032% w/v Calcium Lactate, 0.015% w/v $NaHCO_3$, 0.085% w/v Glucose Anhydrous, and FLO CRS has the following concentrations: NaCl=0.75 mg/L, KCl=0.9 mg/mL and Xylitol=370 mg/mL.

The volume of the composition administered to a patient in need of treatment thereof is sufficient to deliver a therapeutically effective amount of the kappa-carrageenan to the upper airway. In one embodiment, the volume of carrier solution ranges from 50 ml to 350 ml. In a highly preferred embodiment, the volume is between 100 ml to 200 ml. In a highly preferred embodiment, the volume is between 100 mL to 250 mL.

Figure 11:
FIG. 11 is an example of a preferred irrigation device

The composition of the present invention may be applied to the nasal or sinus passages of either or both sides of the face. The volume of carrier solution required to treat the nasal passages and sinus cavities may be administered by the use of a positive pressure irrigation device. Any positive pressure irrigation device may be used to deliver the composition of the present invention. In a highly preferred embodiment the device is a soft squeeze LDPE plastic bottle, dip-tube and a specially designed conical top—such that the end point does not come into contact with the nasal septum. An image of the device is shown in FIG. 11.

The positive pressure device is operated by simply squeezing the bottle until about 100 mL of the solution has been expelled via one nostril into the nasal and paranasal sinus cavities and exits from the opposite nostril. This procedure may then be repeated into the opposite nostril.

The methods and compositions of the present invention are capable of treating tissue inflammation and/or a build-up in mucus which results from acute or chronic disease processes or to clear mucus, dry blood, excised tissue and blood clots resulting from nasal and sinus surgery conducted to facilitate aeration of the paranasal sinuses in patients suffering from acute or chronic sinus disease with or without associated polyposis.

Additional Medicaments, Medications or Therapeutic Agents

Furthermore, the compositions of the present invention may also include one or more topical medications, including but not limited to steroids and antibiotics. The additional topical medications may be necessary for topical treatment in the sinus disease.

Other compounds useful in the preparation of the compositions of the present invention include anti-viral agents, antibiotics, antifungal agents or anti-inflammatory agents and antioxidants.

Diseases or Conditions

The compositions of the present invention may be used to treat any number of diseases or conditions associated with the upper airways. The diseases or conditions which may be treated with the compositions of the present invention include but are not limited to: non allergic rhinitis, allergic rhinitis, acute sinusitis, rhinosinusitis from both allergic and non allergic aetiologies, chronic rhinosinusitis.

As discussed above, these diseases or conditions may be treated by administering a therapeutically effective amount of the compositions of the present invention to a patient in need of treatment thereof.

For example, a large volume (e.g. 100 ml to 200 ml) of the composition of the present invention may be administered via the nostril to the upper airways of the patient via a positive pressure device. The kappa-carrageenan is provided in a sufficient amount to remain in the upper airway to hydrate diseased tissue and to hold topical medications in contact with mucosal surfaces for prolonged periods of time.

EXAMPLES

Experiments were designed to determine the safety of carrageenan as a treatment for diseases and conditions of the upper airways. In addition, experiments were conducted to study the ciliary function and structure after treatment with kappa and iota carrageenan.

The effects of kappa carrageenan in relation to its effect on sinus tissue include: cilial safety, tight junction effects, anti-inflammatory effects and gelation was investigated. The delivery solution containing carrageenan was FLO Sinus Care (Lactated Ringers) or FLO CRS (isotonic with extracellular fluid xylitol with NaCl and KCl).

The results at this point indicate that the kappa Carrageenan is a very safe product to use on sinus tissue and that it will not interfere with any of the normal physiological processes. These experiments and results are discussed below.

1. Experimental Design
1.1 Primary Human Nasal Epithelial Cell Culture

Ethics approval to collect cytological nasal brushings from healthy volunteers was granted from The Queen Elizabeth Hospital Human Ethics Committee. Nasal brushings were collected from consenting participants, exclusions included active smoking, age less than 18 years, systemic diseases, recent upper respiratory tract infection, and symptoms/signs of chronic rhinosinusitis or allergic rhinitis.

Nasal brushings taken from the nasal cavity of volunteers using sterile cytology brushes were immediately transported in Bronchial Epithelial Cell Growth Medium (BEGM) (Lonza, Basel), then washed in phosphate buffered saline (PBS) with centrifugation (1700 rpm for 5 minutes) and resuspended in Clonetics™ B-ALI™ growth medium (Lonza, Basel). Cell samples were then depleted of macrophages in a 100 mm diameter culture plate coated with anti-CD68 (Dako, California) for 20 minutes (Malik et al., (2015) Forum Allergy Rhino). 5 (6): 551-556).

Cell samples were removed from the culture plate and seeded directly onto a type 1 collagen coated T25 flask (Corning, N.Y.). Cells were grown until 80% confluent then harvested for seeding onto collagen coated 6.5 mm permeable transwell inserts with 0.4 µm pores (Corning, N.Y.) at a density of $5 \times 10^4$ cells per well (Lonza Scientific Support, 2011).

Cell cultures were maintained with B-ALI™ growth medium for 3-4 days in a cell incubator at 37° C. with 5% $CO_2$. The apical media was then removed and the basal media replaced with BALI™ differentiation media, media was changed every alternate day. Human nasal epithelial cultures at air liquid interface (HNEC-ALI) were maintained for a minimum of 14 days for development of tight junctions and 28 days for cilia generation (Lee M-K et al, (Drug Deliv. 12(5): 305-311; Fulcher et al., (2005) Human Cell culture Protocols. Springer pages 183-206).

1.2 Carrageenan Sinonasal Solution

Kappa and Iota carrageenan were dissolved in sterile MilliQ (Millipore, Billerica, Mass.) water to a concentration of 0.24% by heating for 2 hours at 80° C. as directed by Marinomed Biotechnologies GmbH. FLO Sinus Care and FLO CRS were suspended in sterile MilliQ at a two-fold concentration. Each of the solutions were filter sterilised and then mixed at a 1:1 ratio to achieve: 0.12% Kappa carrageenan in FLO Sinus Care, 0.12% Iota carrageenan in FLO Sinus Care, 0.12% Kappa carrageenan in FLO CRS, and 0.12% Iota carrageenan in FLO CRS.

Solutions were then stored at room temperature. Sinonasal solutions were then applied to the apical compartment of the cell culture for up to 24 hours to determine the effect on (i) cell viability and inflammation, (ii) mucosal barrier, and (iii) ciliary function and structure.

2. Cell Viability and Inflammation
2.1 Methodology

Supernatant was collected from the basolateral compartment of treated HNEC-ALI after 24 hours of exposure and stored at −20° C. until measurement for cell viability and inflammatory markers. Lactate dehydrogenase (LDH) was measured using a Cytotoxicity Detection Kit (Roche, CA) to determine cell viability. The absorbance of prepared samples was recorded at 490 nm wavelength, and relative viability is calculated using the LDH of negative controls (untreated cells). Total matrix metallopeptidase-2 (MMP-2) secretion was calculated using MMP-2 Human ELISA (Invitrogen, CA), with a minimum detectable level of <0.1 ng/ml. Prepared samples were read with a microtiter plate reader at 450 nm. Results are expressed in ng/ml and as a percentage compared to vehicle control (see equation 1). Interleukin-6 (IL-6) was measured using rat anti-human IL-6 antibody (BD Biosciences, New Jersey) and compared against a human IL-6 standard (BD Biosciences, New Jersey). Samples were measured in a microtiter plate reader at 450 nm, results are expressed as total IL-6 (pg/ml) and compared to control media or vehicle only control.

$$MMP2(\text{fold change}) = \frac{MMP2 \text{ total}}{MMP2 \text{ baseline}} \quad \text{Equation 1}$$

2.2. Results: Lactate Dehydrogenase Assay

LDH measurement expressed as fold change against the control media as a negative control showed mean (±SD) values: FLO Sinus Care (FLO) 1.122 (±0.1283), FLO plus 0.12% Kappa carrageenan (FLO+Kappa) 0.9512 (±0.1679), FLO plus 0.12% Iota carrageenan (FLO+Iota) 1.003 (±0.1582), FLO CRS 0.946 (±0.1526), FLO CRS plus 0.12% Kappa carrageenan (CRS+Kappa) 1.001 (±0.1585), FLO CRS plus 0.12% Iota carrageenan (CRS+Iota) 0.9731 (±0.154) as shown in FIG. 1A).

Figure 1B:
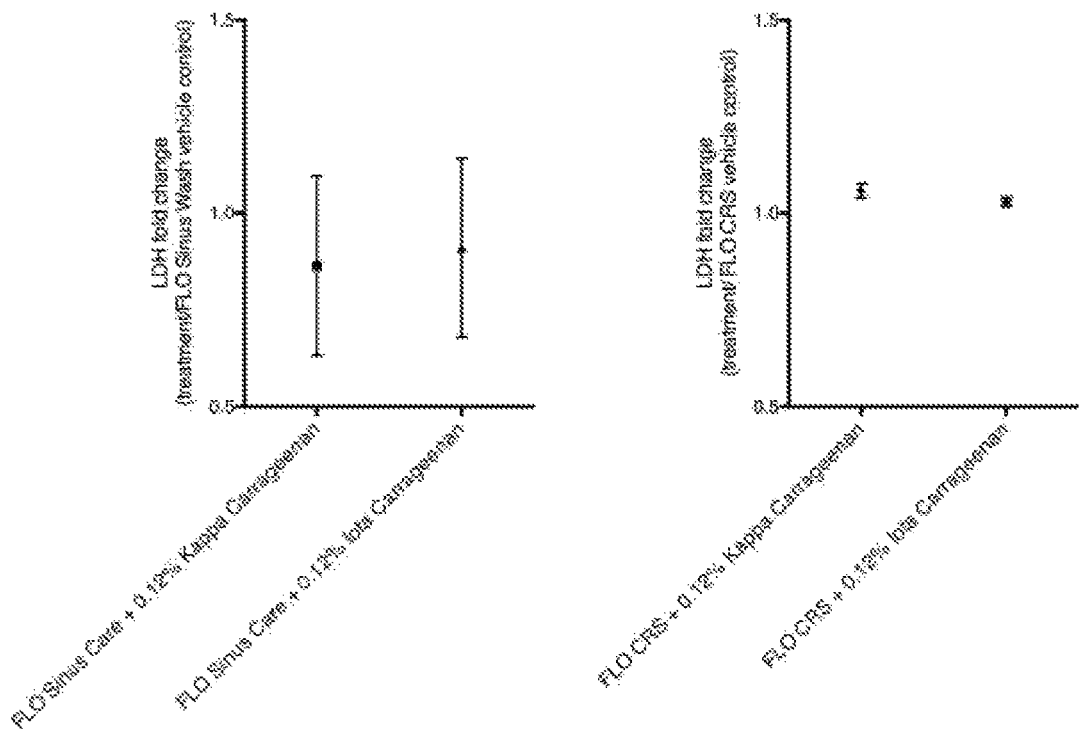
FIG. 1B are graphs showing lactate dehydrogenase expression in the supernatant of human nasal epithelial cells exposed to 24 hours of carrageenans in FLO sinus Care or FLO CRS solution. Expressed as fold change compared to vehicle only control (vehicle control=1); error bars represent standard deviation.

When LDH was compared against the vehicle only control (FLO or CRS) fold change mean (±SD) values were: FLO+Kappa 0.8652 (±0.2314), FLO+Iota 0.9115 (±0.2304), CRS+Kappa 1.058 (±0.01793) and CRS+Iota 1.029 (±0.01218) as shown in FIG. 1B.

2.3 Results: Matrix Metallopeptidase-2 ELISA

Figure 2A:
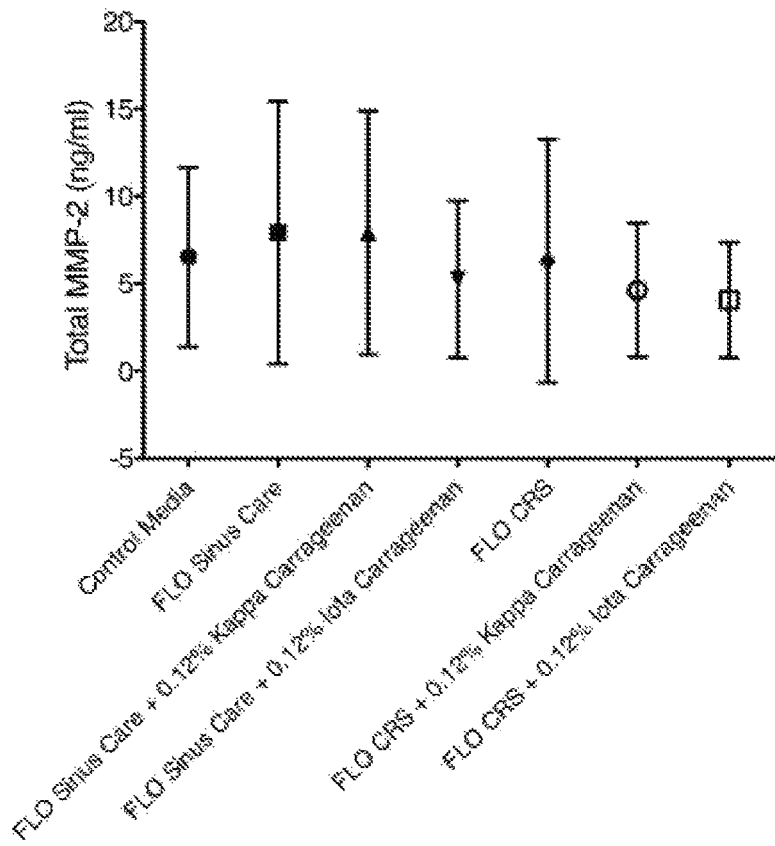
FIG. 2A is a graph showing matrix metallopeptidase-2 expression in the supernatant of human nasal epithelial cells exposed to 24 hours of carrageenan in FLO Sinus Care or FLO CRS solution. Expressed as total (ng/ml); error bars represent standard deviation.

Basal MMP-2 ELISA measurement showed mean (±SD) ng/ml values: control media 6.531 ng/ml (±5.138), FLO 7.924 ng/ml (±7.513), FLO+Kappa 7.907 ng/ml (±6.974), FLO+Iota 5.247 ng/ml (±4.503), CRS 6.3 ng/ml (±6.961), CRS+Kappa 4.626 ng/ml (±3.836), CRS+Iota 4.054 (±3.309) as shown in FIG. 2A.

Figure 2B:
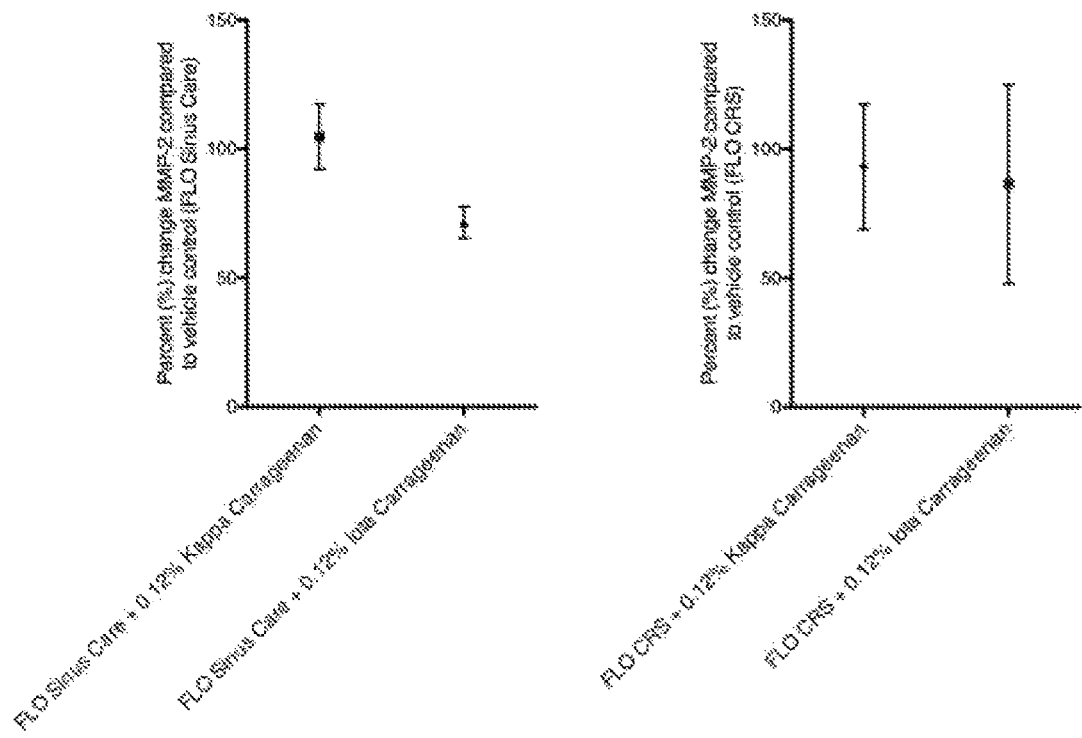
FIG. 2B are graphs showing matrix metallopeptidase-2 expression in the supernatant of human nasal epithelial cells exposed to 24 hours of carrageenan in FLO Sinus Care or FLO CRS solution. Expressed as percentage (%) of vehicle only control (vehicle only=100%); error bars represent standard deviation.

When MMp-2 was compared as a percentage of the vehicle only control the mean (±SD) were: FLO+Kappa 104.7% ((±12.64), FLO+Iota 71.75% (±6.092), CRS+Kappa 93.17% (±24.18), and CRS+Iota 86.5% (±38.51) as shown in FIG. 2B.

2.4 Results: Interleukin-6 ELISA

Figure 3A:
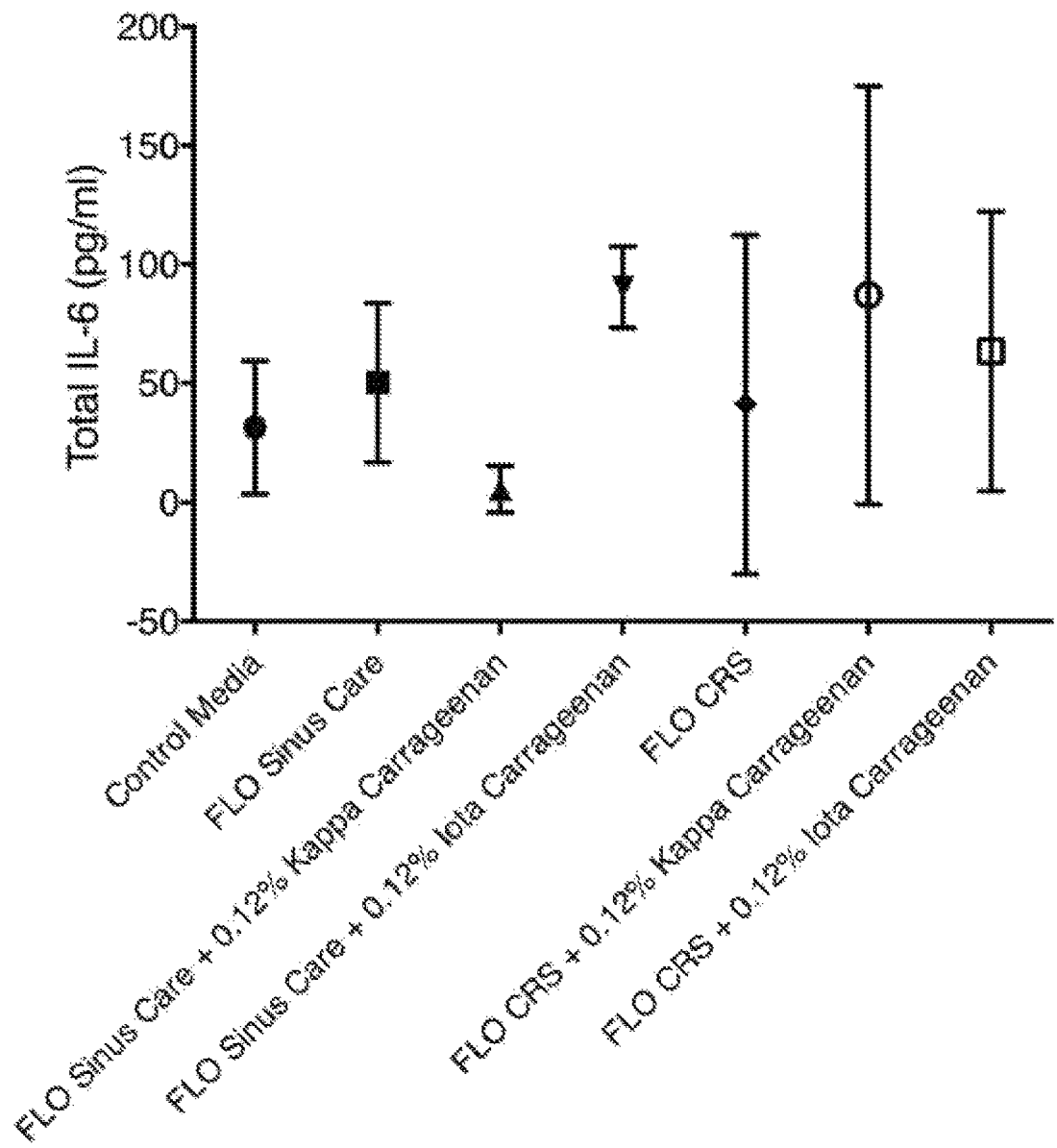
FIG. 3A are graphs showing Interleukin-6 expression in the supernatant of human nasal epithelial cells exposed to 24 hours of carrageenan in FLO Sinus Care or FLO CRS solution. Expressed as total IL-6 (pg/ml); error bars represent standard deviation.
Figure 3B:
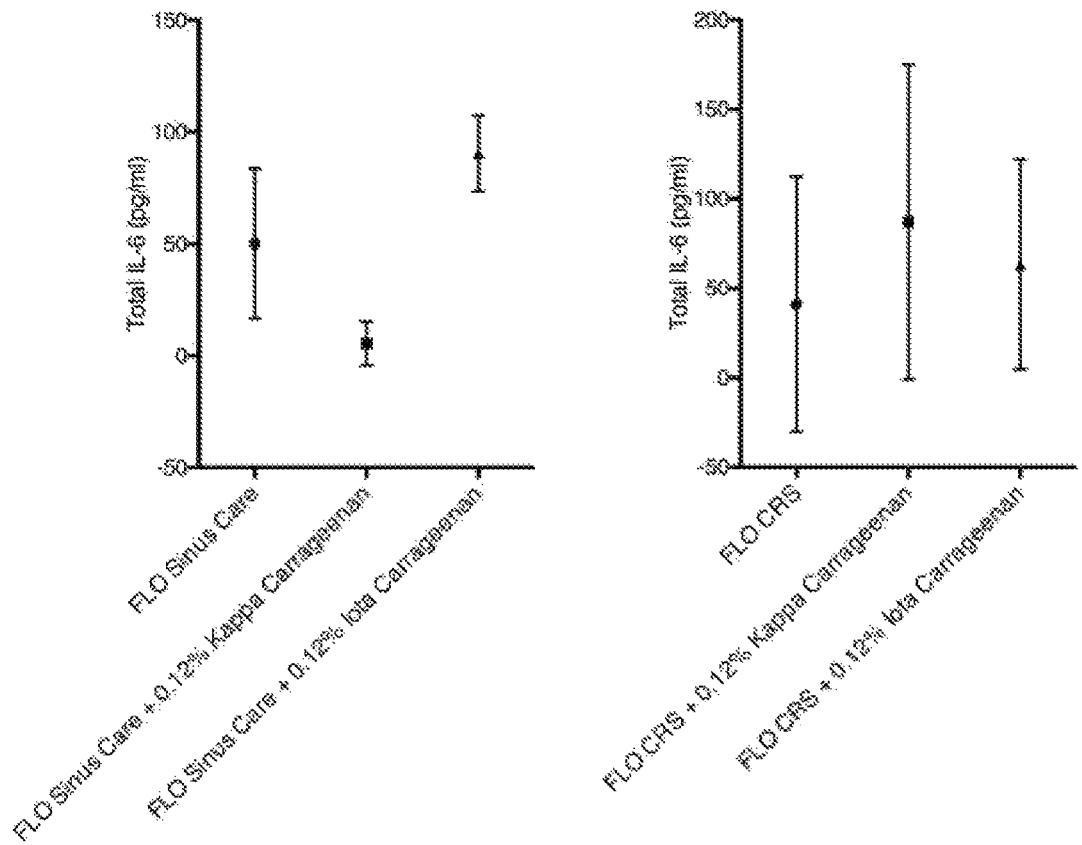
FIG. 3B are graphs showing Interleukin-6 expression in the supernatant of human nasal epithelial cells exposed to 24 hours of carrageenan in FLO Sinus Care or FLO CRS solution, shown with vehicle only control. Expressed as total IL-6 (pg/ml); error bars represent standard deviation

Basal IL-6 ELISA measurement showed mean (±SD) pg/ml values: control media 31.42 pg/ml (±27.89), FLO 50.28 pg/ml (±33.39), FLO+Kappa 5.626 pg/ml (±9.745), FLO+Iota 90.39 pg/ml (±17.04)m CRS 41.12 pg/ml (±71.21)m CRS+Kappa 87.16 pg/ml (±87.9), CRS+Iota 63.49 pg/ml (±58.69) as shown in FIGS. 3A and 3B.

In conclusion, expression of inflammatory markers MMP-2 (gelatinase) and IL-6 (cytokine) was not increase following exposure to carrageenan when compared to vehicle only control, suggesting that carrageenan is not pro-inflammatory.

Furthermore, neither Kappa- nor Iota carrageenan decreased cell viability.

Finally, based on the design of this study, further experiments are required to confirm that if carrageenan is anti-inflammatory, as the cell culture used was modelled on healthy human nasal epithelium. Future studies using an inflammatory stimulation of normal cell cultures or to define a new cohort of patients with measurable increases in inflammatory markers that are maintained in vitro are planned.

3. Mucosal Barrier Function 3.1. Methodology

Transepithelial electrical resistance (TEER) was measured using an EVOM2 epithelial voltohmmeter (World Precision Instruments, FL) and results were expressed in Ohm as the raw value, or as a relative change to the initial reading. TEER values were only taken from cultures showing >400 ohm/cm$^2$ (equivalent to >1200 ohm in a 0.33 cm2 transwell membrane). TEER was initially measured on all HNEC-ALI transwell samples with cell media apically and basally, following this the apical media was removed and replaced with the corresponding control or treatment.

Time points measured included 0, 12 and 24 hours and then an additional measurement at 24 hours with the apical treatment removed and replaced by cell media to adjust for conductivity issues due to the low electrolyte concentration of CRS FLO solution. All measurements were taken on a 37° C. stage. The paracellular permeability of the HNEC-ALI cultures was assessed following 24 hours of Carrageenan exposure. A 4 kDa fluorescein isothiocyanate (FITC) dextran (Sigma-Aldrich, Saint Louis) was added to the apical compartment to a concentration of 3 mg/ml, samples were then taken from the basolateral compartment after 2 hours. The amount of passaged dextran was measured using a Fluostar Optima 96 well fluorescence microplate reader using wavelengths 485 nm and 520 nm for excitation and emission respectively. Results assumed sink conditions of FITC dextran transfer and calculated according to the following (see equation 2).(3)

$$Papp = \left(\frac{dQ}{dt}\right) \times \frac{1}{AC_0} \quad \text{Equation 2}$$

Papp is the apparent permeability coefficient (cm/s), dQ/dt (mg/s) is the rate of transfer of the FITC dextran to the basolateral compartment, A (cm3) is the surface area of the transwell membrane, and CO (mg/ml) is the starting drug concentration of the apical compartment. Fold changes were calculated from Papp values (see equation 3).

$$Papp \text{ (fold change)} = \frac{Papp(\text{sample})}{Papp(\text{control})} \quad \text{Equation 3}$$

Papp of the Carrageenan treated samples were either compared to the control media or vehicle control.

Immunocytochemistry of the F-actin cytoskeleton was performed by fixing samples in 2% paraformaldehyde for 15 minutes, samples were then washed with phosphate buffered saline, dried and stored at −4□ C. Fixed specimens were permeabilised with 0.1% Triton X-100 in PBS while kept on ice for 15 minutes, washed three times in PBS, and protein block (Dako, California) was applied. Samples were again washed three times in PBS, and incubated with 1:100 Alexa Fluor 488 phalloidin (Life Technologies, California) for 45 minutes, and then washed three times in PBS. DAPI (Sigma, St Louis) was added for 10 minutes followed by three PBS washes and then mounted on glass slides. Confocal microscopy was performed using a Zeiss LSM 700 inverted microscope. Phalloidin and DAPI were excited with 495 nm and 364 nm, and emission 518 nm and 454 nm respectively.

3.2 Results: Trans-Epithelial Electrical Resistance (TEER)

Figure 4A:
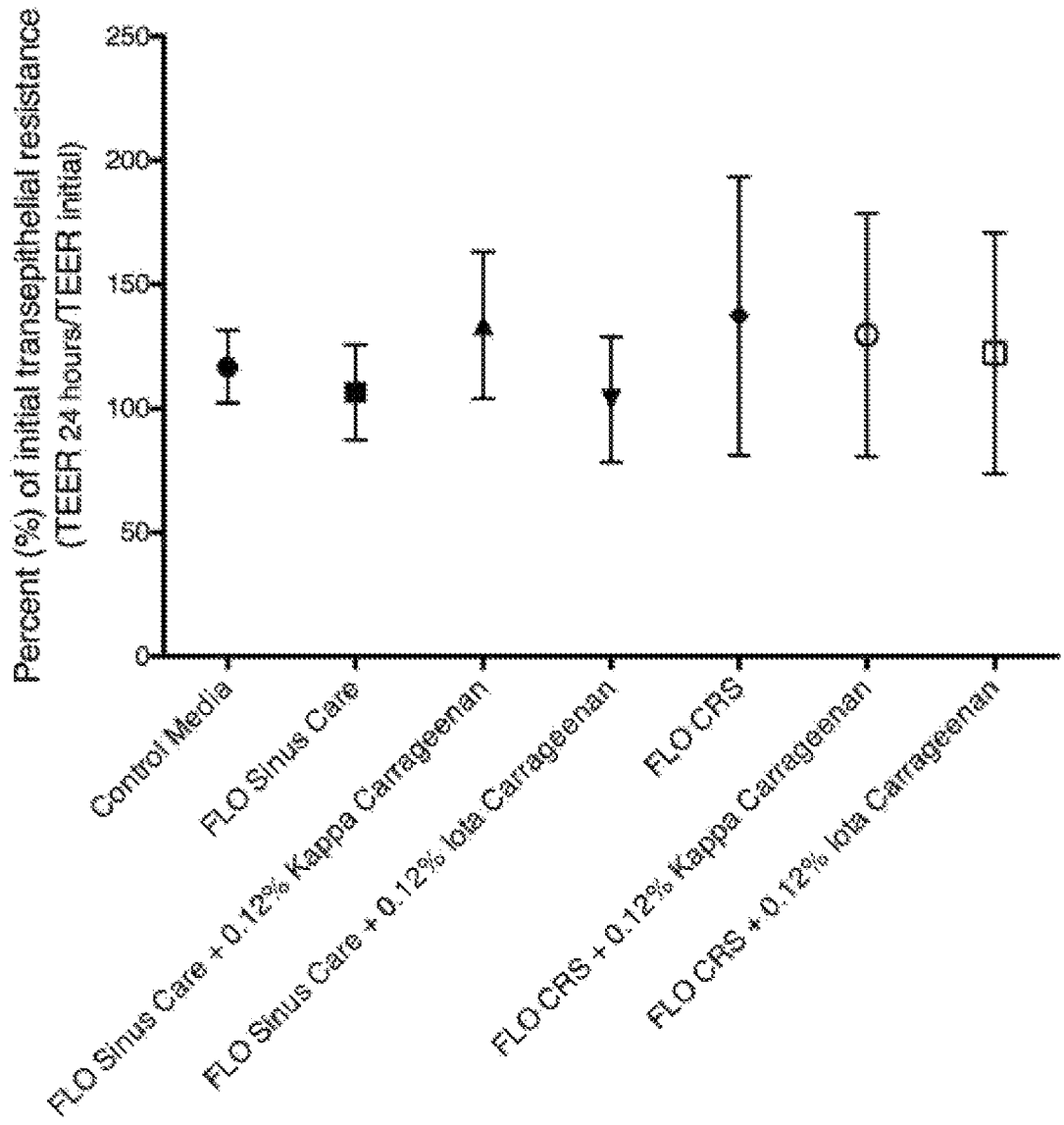
FIG. 4A is a graph showing percentage of initial transepithelial electrical resistance of air liquid interface human nasal epithelial cells exposed to 24 hours of Kappa and Iota carrageenan in either FLO Sinus Care or FLO CRS solution, measure in cell buffer

Trans-epithelial electrical resistance (TEER) of treated HNEC-ALI cultures expressed as a percentage of the initial TEER at 24 hours showed mean (●}SD) values: control media 116.9% (●}14.59), FLO 106.5% (●}19.14), FLO+Kappa 133.5% (●}29.58), FLO+Iota 103.6% (●}25.23), CRS 137.3% (●}56.16), CRS+Kappa 184.3% (●}133.9), CRS+Iota 122.3% (●}48.59) (FIG. 4A). Initial and 24 hour measurements were taken in identical cell buffer and calculated seen below (see equation 4).

$$\text{TEER (\% change)} = (\text{TEER (24 hours)})/(\text{TEER (initial)}) \times 100 \quad \text{Equation 4:}$$

Figure 4B:
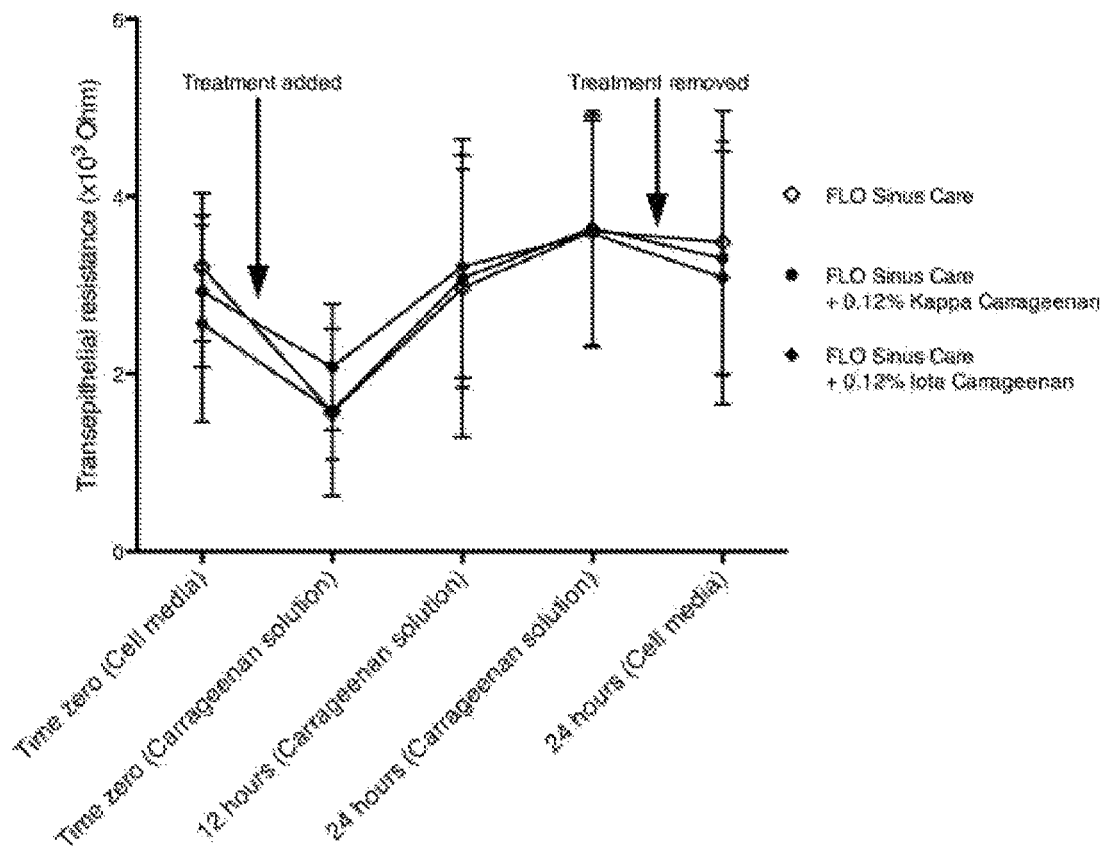
FIG. 4B is a graph showing transepithelial resistance changes of air liquid interface human nasal epithelial cell cultures exposed to Kappa and Iota carrageenan in FLO Sinus Care. Measurements taken in cell media and carrageenan solution at baseline, 12 hours and 24 hours
Figure 4C:
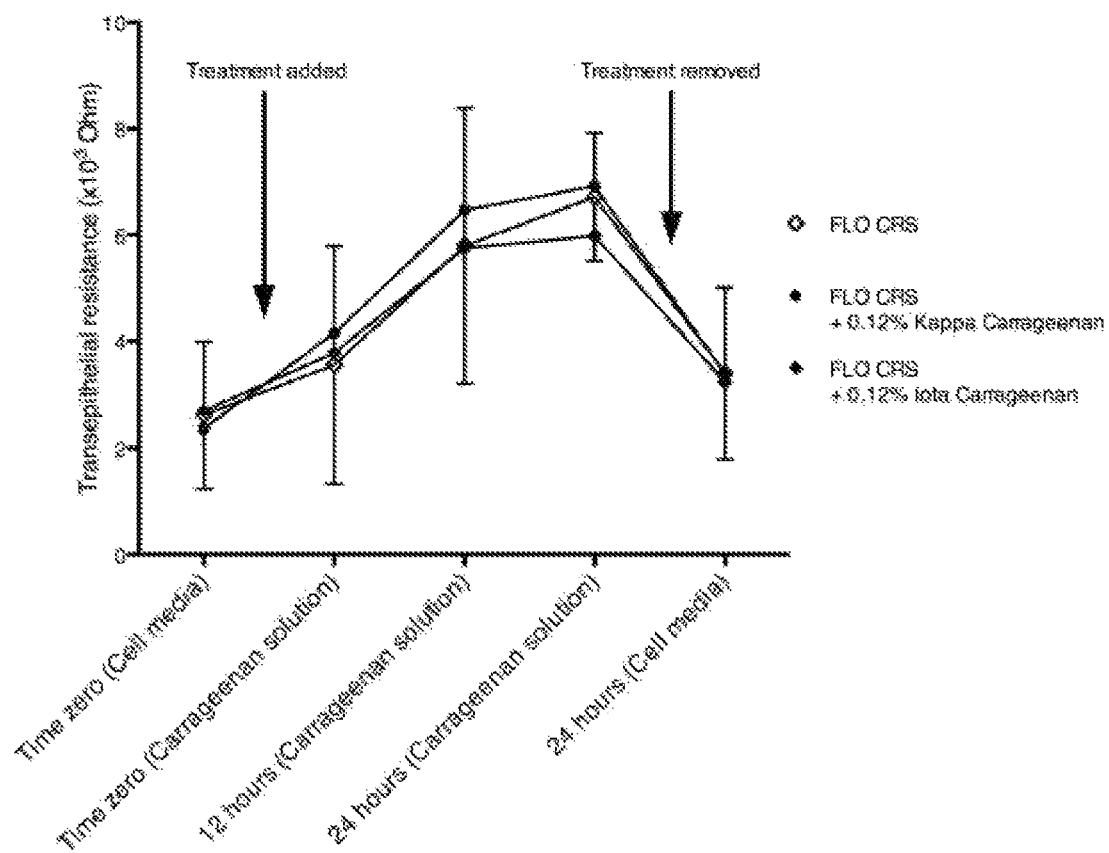
FIG. 4C is a graph showing transepithelial resistance changes of air liquid interface human nasal epithelial cell cultures exposed to Kappa and Iota carrageenan in FLO CRS solution. Measurements taken in cell media and carrageenan solution at baseline, 12 hours and 24 hours

TEER measurements taken with the treatment solution apically are also demonstrated (see FIGS. 4B and 4C), but show greater variability which may be artefact due to the low ion concentrations of FLO CRS solution which impedes resistance. TEER is expressed as a raw value (Ohm).

Figure 5A:
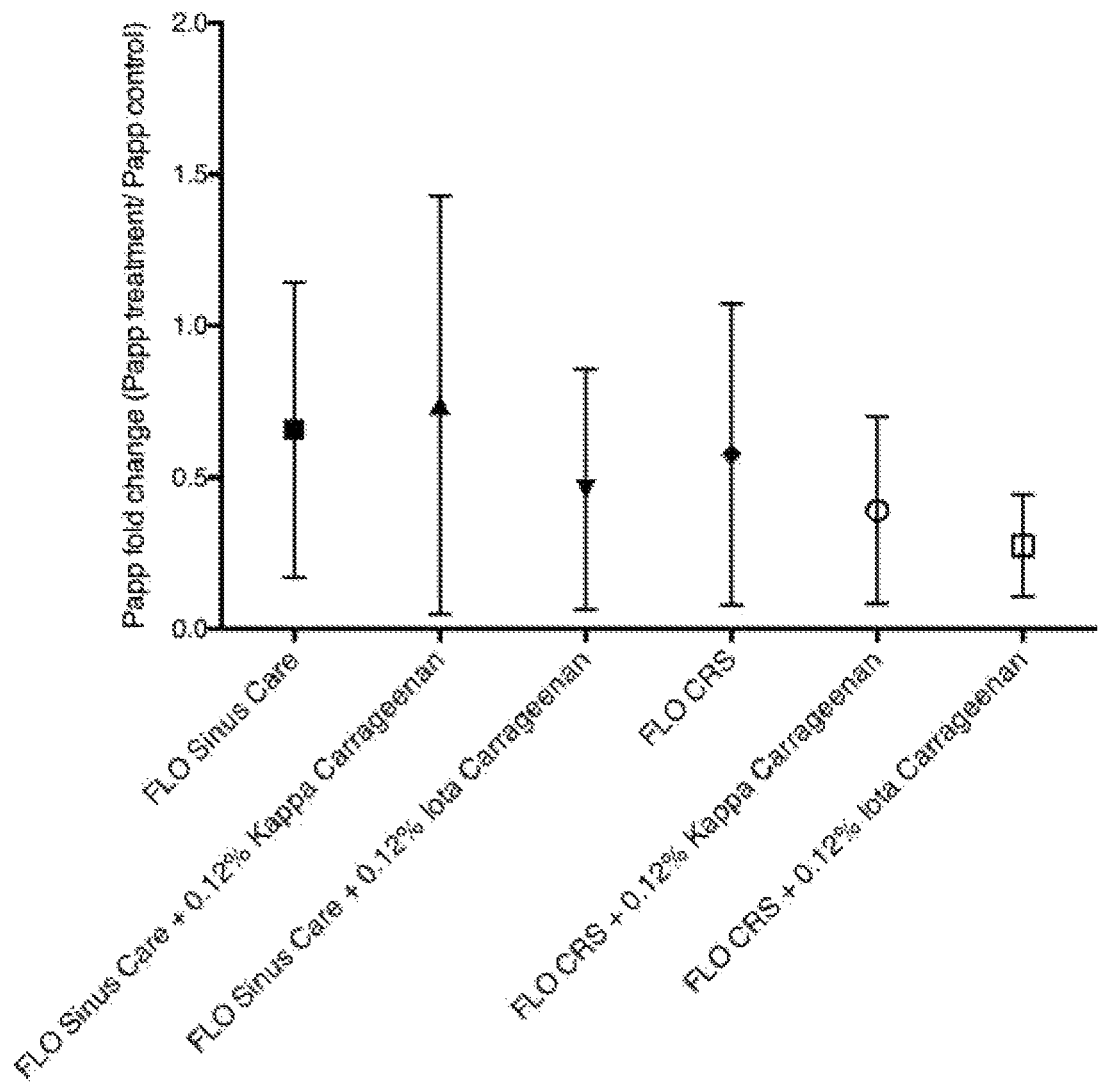
FIG. 5A is a graph showing paracellular permeability of air liquid interface human nasal epithelial cell culture exposed to 24 hours of Kappa or Iota carrageenan in either FLO Sinus Care or FLO CRS solution, expressed as fold change compared to control media (control media=1)

Apparent paracellular permeability (Papp) was measured following 24 hours of exposure to Kappa or Iota carrageenan in FLO or FLO CRS solution. When compared to the Papp of HNEC-ALI exposed to control media the mean (±SD) fold change values were: FLO 0.6562 (±0.6905), FLO+Iota (±0.3961), CRS 0.5751 (±0.4978), CRS+Kappa 0.3913 (±0.0384), CRS+Iota 0.2756 (±0.1691) as shown in FIG. 5A.

Figure 5B:
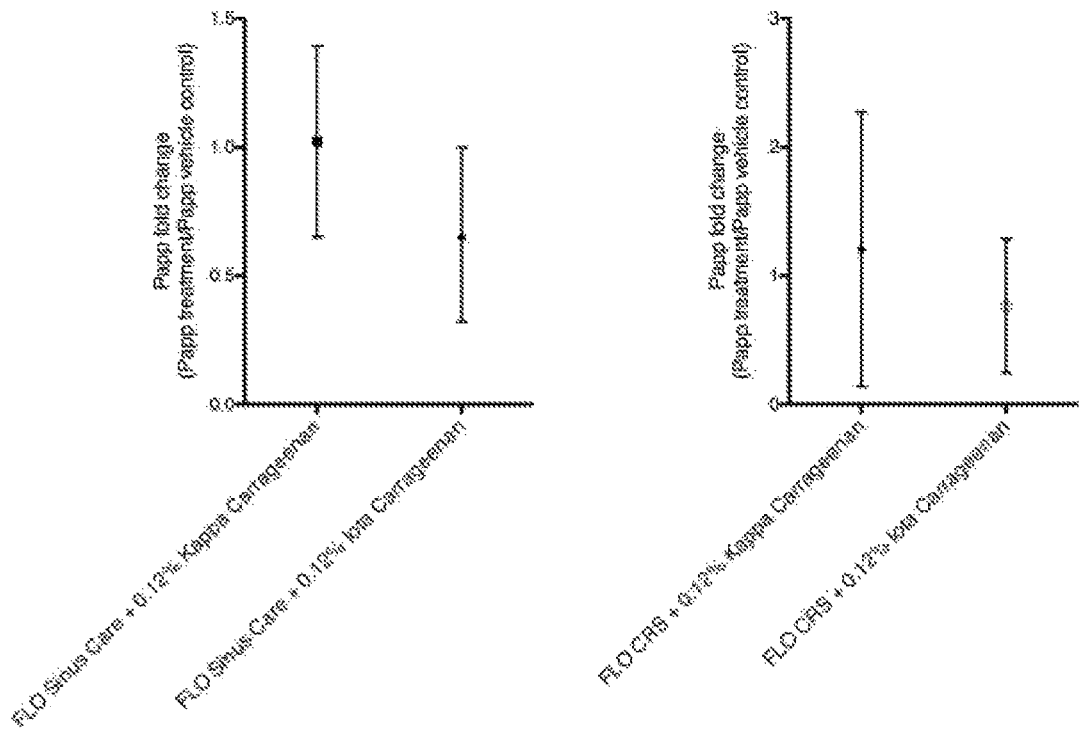
FIG. 5B are graphs showing paracellular permeability of air liquid interface human nasal epithelial cell culture exposed to 24 hours of Kappa or Iota carrageenan in either FLO Sinus Care or FLO CRS solution, expressed as fold change of vehicle control (vehicle control=1)

Papp of HNEC-ALI when compared against the vehicle only control showed mean (±SD) fole change values of: FLO+Kappa 1.0023 (±0.3718), FLO+Iota 0.6605 (±0.3397), CRS+Kappa 1.205 (±1.067), CRS+Iota 0.7638 (±0.5211) as shown in FIG. 5B.

3.3 Results: Actin Cytoskeleton Immunocytochemistry

Figure 6:
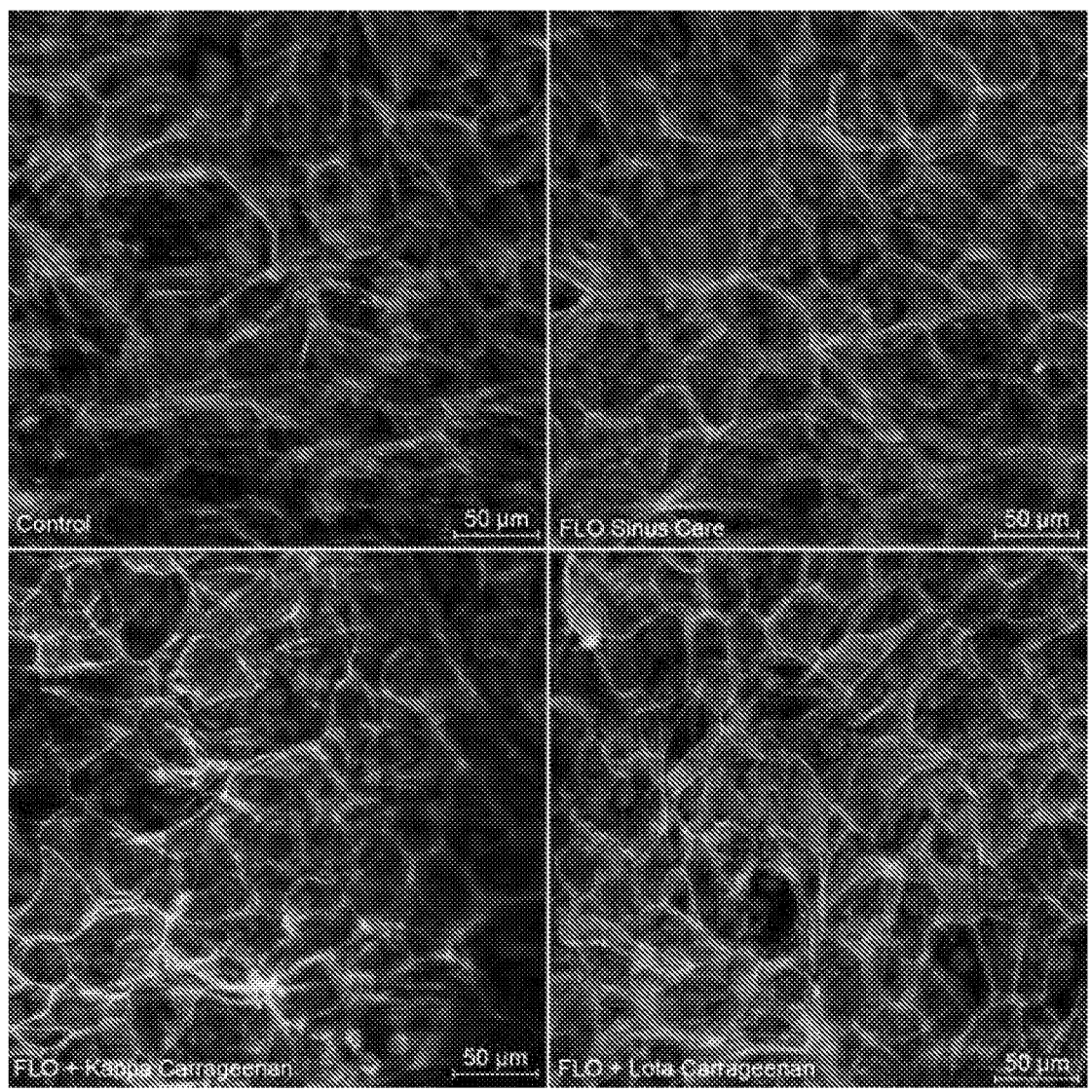
FIG. 6 are photos of cytoplasmic staining of actin, showing the effects of 24 hour exposure of 0.12% Kappa or Iota carrageenan in FLO Sinus Care on the actin cytoskeleton of air liquid interface human nasal epithelial cell cultures. F-action was visualised with phalloidin (green) and the cell nucleus with DAPI (blue)
Figure 7:
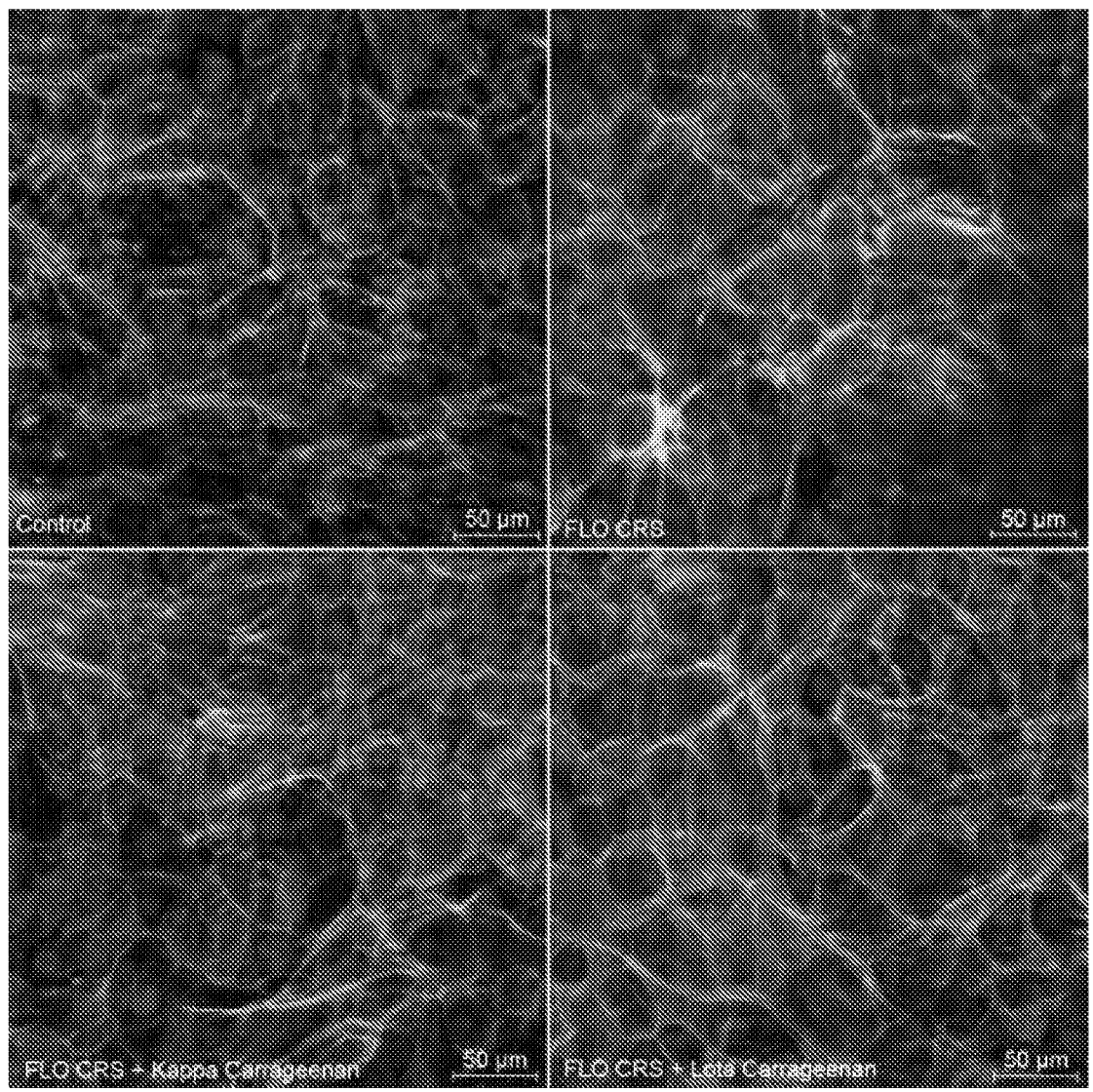
FIG. 7 are photos showing the effects of 24 hour exposure of 0.12% Kappa or Iota carrageenan in FLO CRS solution on the actin cytoskeleton of air liquid interface human nasal epithelial cells cultures. F-actin was visualised with phalloidin (green) and the cell nucleus with DAPI (blue)

The morphological characteristics of the HNEC-ALI specifically F-actin localisation was assessed in cultures exposed to Kappa and Iota carrageenan. The actin cytoskeleton is important in maintaining cell polarity, vesicle transport and intimately associated with the cell junction complete including tight junctions and adherens junctions. Confocal imaging showed non loss of actin cables, distribution or change in cell shape. There was no specific increase in the cytoplasmic staining of actin as shown in FIG. 6 and FIG. 7.

In conclusion, the mucosal barrier function is not reduced by the exposure to carrageenan and there is no obvious disruption of the normal barrier as measure by TEER or Papp in healthy human epithelial cells. However, in tissue from diseased patients there was an increase in TEER in tissue exposed to FLO CRS and also to FLO CRS with carrageenan, but no disruption to normal barrier. These results are shown in Section 6 below.

There is a trend for the Iota carrageenan to decrease the Papp of HNEC-ALI to 4 kDa dextran, which may be related to a direct action on a component of the junctional barrier, actin cytoskeleton or due to the large molecular size compound hence limiting the permeability.

Although there was no quantification of the F-actin staining there appears to be an increase in the apical F-actin strand complexity of the carrageenan exposed specimens, primarily the Iota carrageenan.

4. Cilia Function and Structure 4.1 Methodology

Ciliary beat frequency (CBF) of HNEC-ALI cultures were assessed using a ×20=objective, and ×1.5 magnification on an inverted microscope (Olympus, Tokyo). Video was recorded using a Model Basler acA645-100 µm USB3 camera (Basler AG, Ahrensburg, Germany) at 100 frames per second at a resolution of 640×480 pixels. The recorded video samples were analysed using the Sisson-Ammons Video Analysis (SAVA) system (Sisson et al., (2003) 211(2): 103-111). All measurements were taken at room temperature of 22° C.

A baseline CBF was taken prior to addition of the experimental conditions, initially HNEC-ALI cultures were washed with 100 µl of PBS then 40 µl of room temperature PBS was added to the apical compartment. Baseline measurements were taken from two separate regions from each culture. The apical PBS was removed and either the control media, vehicle only control or carrageenan containing solution was added. Sequential readings were taken every 5 minutes for the first 20 minutes to assess for any early stimulation/slowing of the CBF, reading were also taken at 6 and 24 hours.

Results are expressed as the mean CBF (Hz) and also as a percentile change when compared to baseline. Scanning electron microscopy (SEM) specimens were fixed in a solution of 4% paraformaldehyde and 1.25% glutaraldehyde in phosphate-buffered solution and stored at 4° C. Samples were washed in buffer and underwent serial dehydration with ethanol, followed by immersion in 1:1 mixture of hexamethyldisilazane (HMDS) and then in 100% HMDS. Specimens were mounted on aluminium stubs and carbon coated. Images were taken with a Philips XL30 Filed Emission Gun SEM (Philips, the Netherlands) at an accelerated voltage of 5 kV under vacuum (Mallants et al., (2009), J. Pharm. Pharmacol. 161(7): 883-890); Murphy et al., (2015) Ophthal Plat Reconstr Surg. 31(5): 396-400).

4.2. Results: Ciliary Beat Frequency—Preliminary: Based on Two Replicates

Figure 8A:
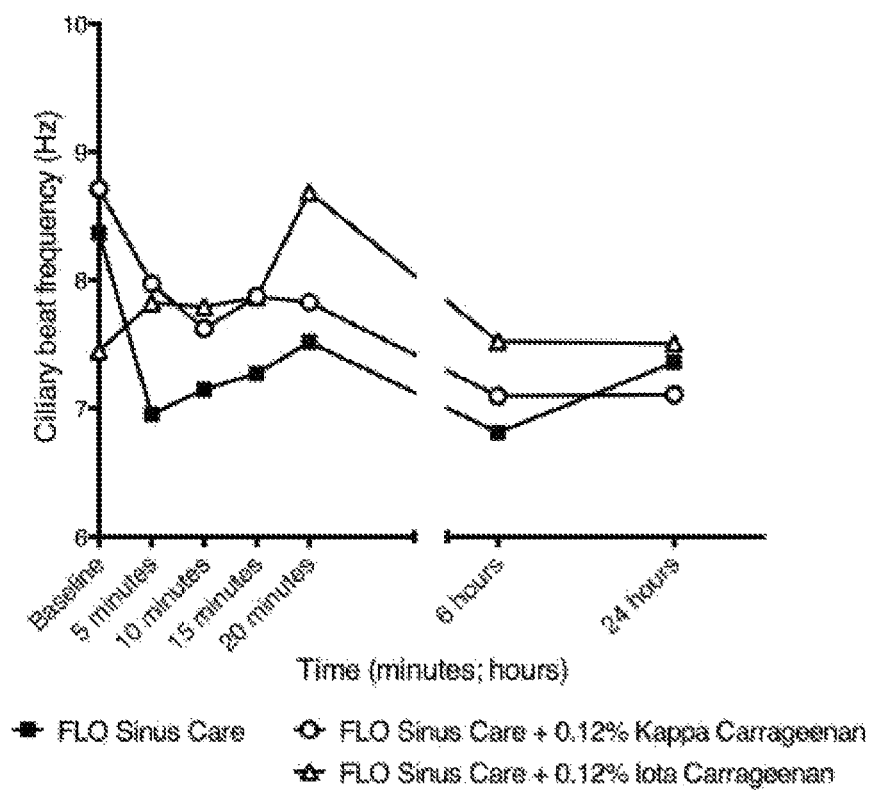
FIG. 8A are graphs showing ciliary beat frequency of air liquid interface human nasal epithelial cell cultures exposed to Kappa or Iota carrageenan in FLO Sinus Care or FLO CRS solution. Measurements represent the mean (Hz) over the time points: 5 minutes, 10 minutes, 15, minutes, 20 minutes, 6 hours and 12 hours FIG. 8B are graphs showing ciliary beat frequency of air liquid interface human nasal epithelial cell cultures exposed to Kappa or Iota carrageenan in FLO Sinus Care or FLO CRS solution. Measurements represent the mean change from baseline (%; $CBF_{t=x}/CBF_{baseline}$) over the time points: 5 minutes, 10 minutes, 15, minutes, 20 minutes, 6 hours and 12 hours FIG. 9 are scanning electron micrographs (10000×) of human nasal epithelial cell cultures exposed to Kappa or Iota carrageenan in FLO Sinus Care solution showing cilia surface structure FIG. 10 are scanning electron micrographs (10000×) of human nasal epithelial cell cultures exposed to Kappa or Iota carrageenan in FLO CRS solution showing cilia surface structure
Figure 8A:
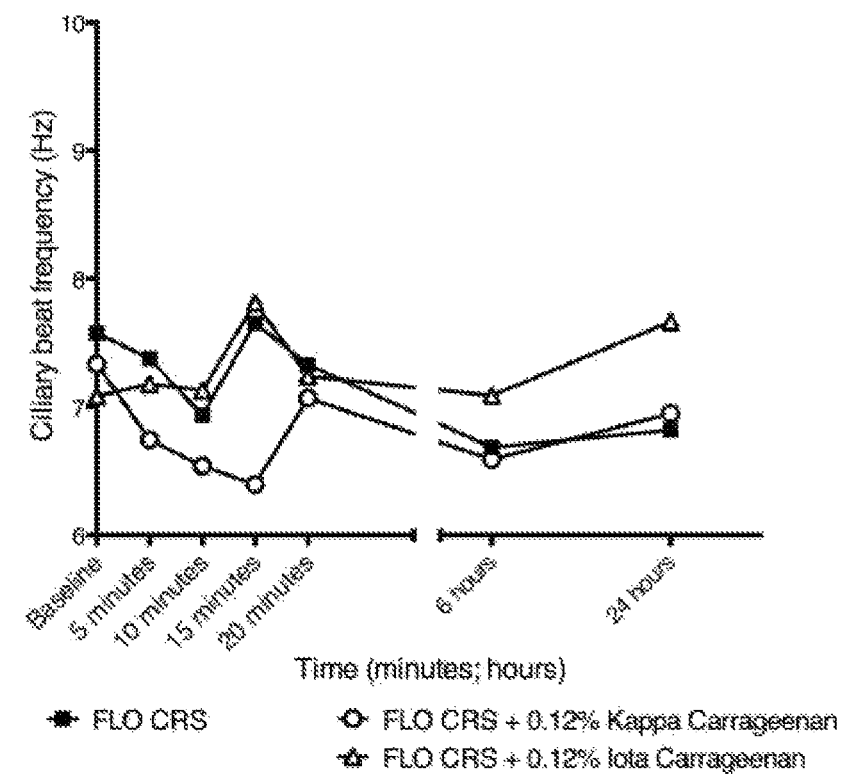

Ciliary beat frequency measurement showed the following raw values (FIG. 8A): FLO baseline (8.06, 8.67 Hz), 5 minutes (7.93, 5.98 Hz), 10 minutes (7.42, 6.87 Hz), 15 minutes (8.22, 6.32 Hz), 20 minutes (7.46, 7.57 Hz), 6 hours (6.82, 6.80 Hz), 24 hours (8.15, 6.56 Hz); FLO+Kappa baseline (8.37, 9.05 Hz), 5 minutes (8.16, 7.78 Hz), 10 minutes (7.88, 7.36 Hz), 15 minutes (8.08, 7.66 Hz), 20 minutes (7.86, 7.79 Hz), 6 hours (6.6, 7.59 Hz), 24 hours (7.27, 6.94 Hz); FLO+Iota baseline (8.17, 6.72 Hz), 5 minutes (8.94, 6.7 Hz), 10 minutes (8.43, 7.15 Hz), 15 minutes (8.17, 7.56 Hz), 20 minutes (9.14, 8.23 Hz), 6 hours (8.0, 7.04 Hz), 24 hours (7.9, 7.11 Hz); CRS baseline (7.1, 8.05 Hz), 5 minutes (7.18, 7.58 Hz), 10 minutes (6.64, 7.23 Hz), 15 minutes (7.32, 7.99 Hz), 20 minutes (7.32, 7.34 Hz), 6 hours (6.05, 7.32 Hz), 24 hours (6.35, 7.29 Hz); CRS+Kappa baseline (6.98, 7.69 Hz), 5 minutes (6.65, 6.84 Hz), 10 minutes (6.89, 6.19 Hz), 15 minutes (6.36, 6.43 Hz), 20 minutes (6.93, 7.21 Hz), 6 hours (6.53, 6.65 Hz), 24 hours (7.11, 6.79 Hz); CRS+Iota baseline (7.75, 6.42 Hz), 5 minutes (7.15, 7.21 Hz), 10 minutes (7.16, 7.1 Hz), 15 minutes (7.55, 8.08 Hz), 20 minutes (7.09, 7.39 Hz), 6 hours (6.95, 7.23 Hz), 24 hours (8.55, 6.78 Hz).

Figure 8B:
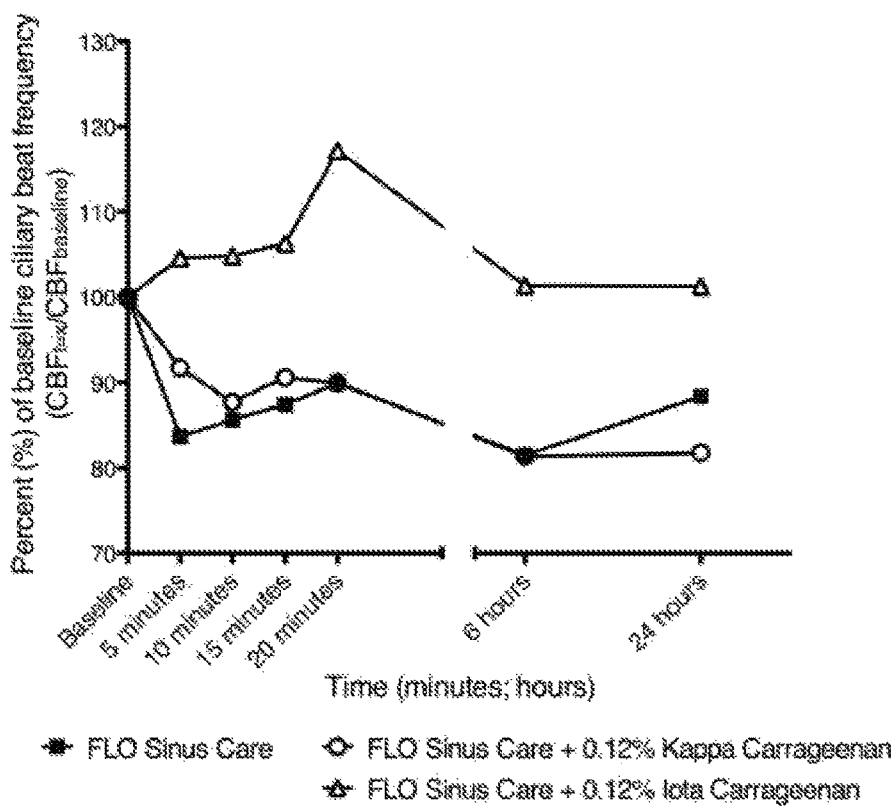
Figure 8B:
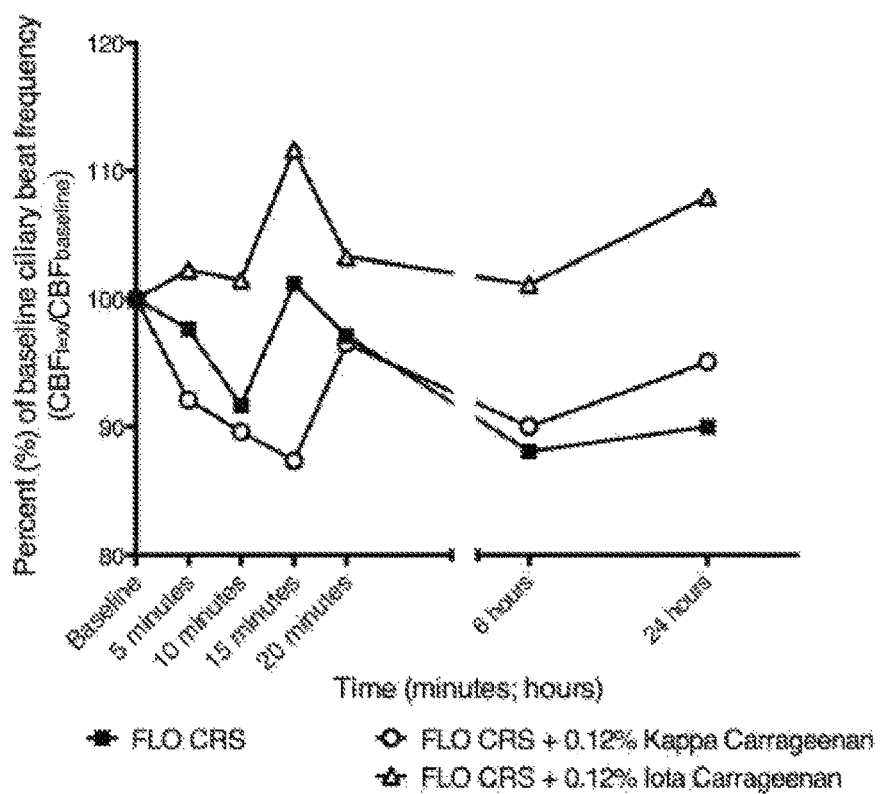
Figure 18:
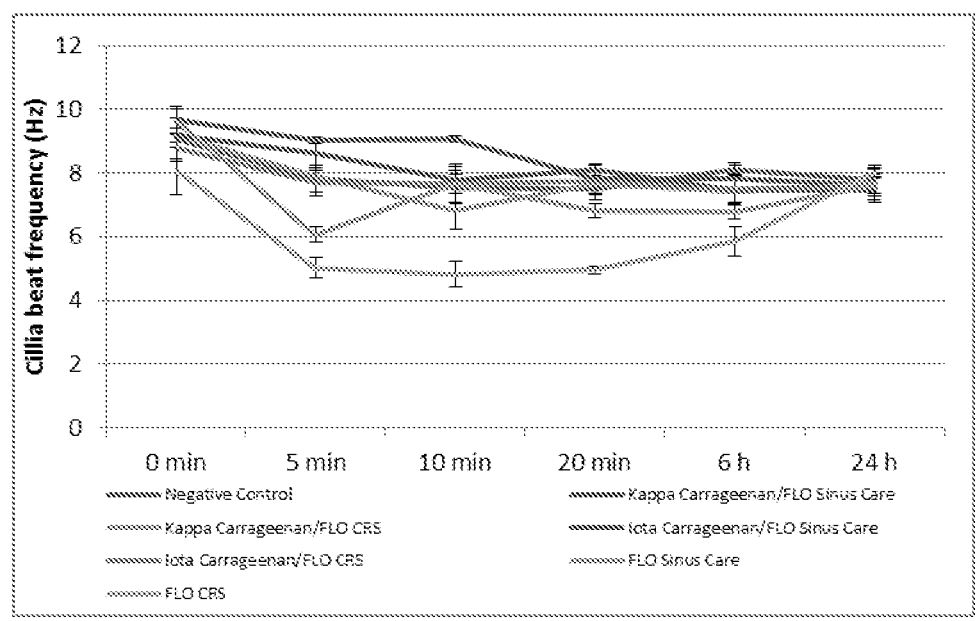
FIG. 18 is a graph showing ciliary beat frequency of air liquid interface human nasal epithelial cell exposed to Kappa or Iota carrageenan in FLO Sinus Care or FLO CRS solution. Measurements represent the mean (Hz) over the time points: 5 minutes, 10 minutes, 20 minutes, 6 hours, and 24 hours. The values are shown as means±SEM for n=3.

CBF changes over time were compared against the baseline measurement showing a trend for Iota carrageenan to stimulate the cilia within 20 minutes and up to 24 hours as shown in FIG. 8B. The effects of these solutions on the ciliary beat frequency of cells from patients with CRS indicate that FLO CRS initially causes a decrease in CBF at 5 minutes which returns to normal in 24 hours (see Section 6 below). This effect is prevented by the addition of Kappa carrageenan. FLO Sinus Care has a similar effect on CBF of diseased tissue culture, which once again is reversed with the addition of Kappa carrageenan. This indicates that Kappa carrageenan is protective of cilia physiology. The results are shown in FIG. 18 and referred to in Section 6.17 below).

Figure 9:
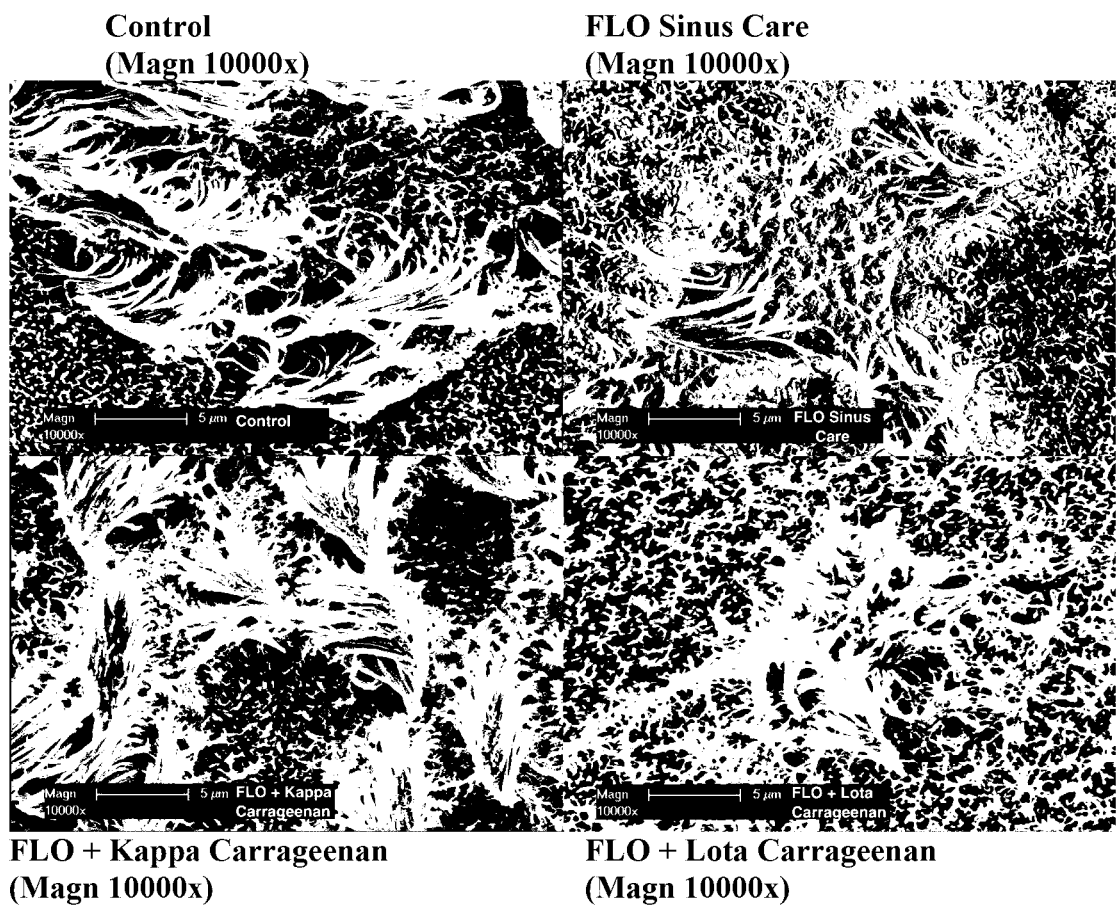
Figure 10:
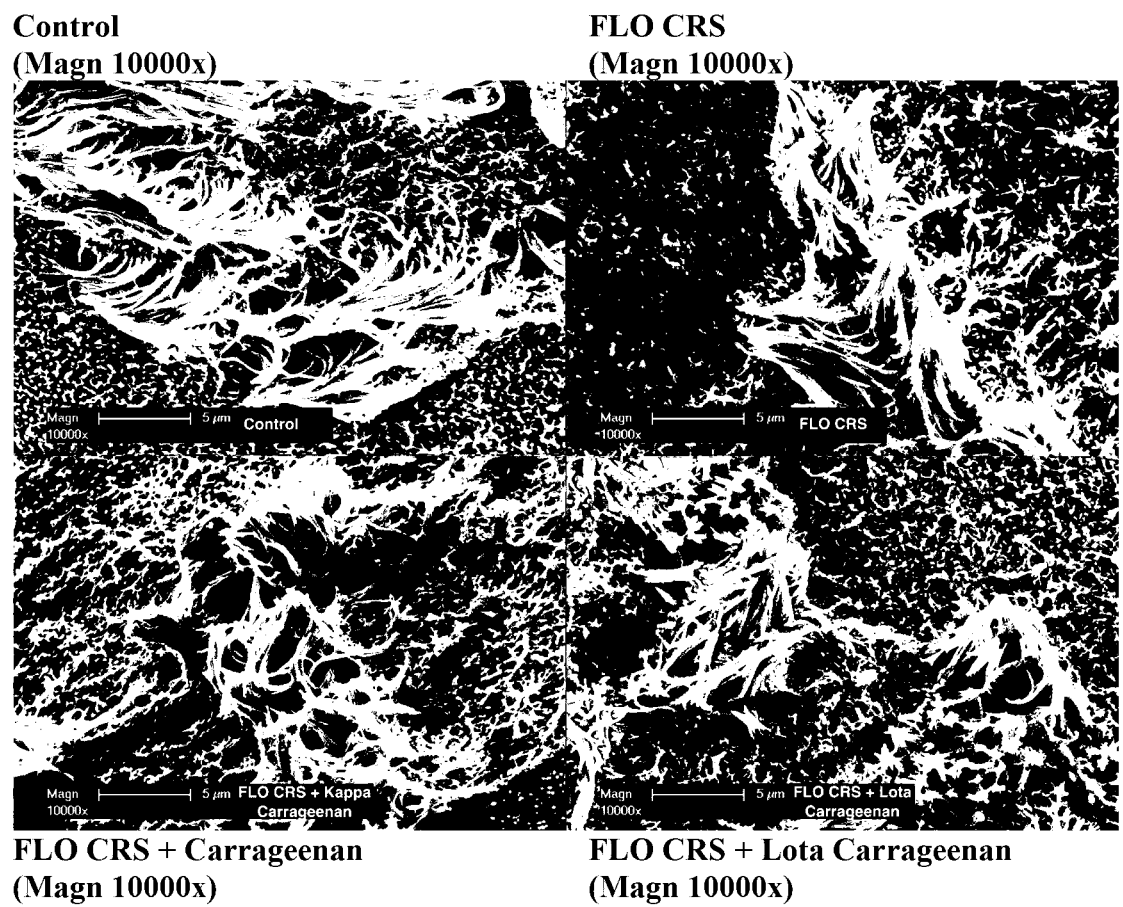

The morphological characteristics of the ciliated epithelial cells were observed by scanning electron microscopy at 10,000× magnification. Normal ciliated cells and surrounding microvilli were observed in all experimental conditions as demonstrated (see FIGS. 9 and 10). Large field analysis was not performed on this occasion due to distortion of the cell layer during processing.

Based on results from duplicate experiments, the current data on healthy tissue cultures shows a trend that Iota carrageenan may enhance the CBF above that of FLO or FLO CRS solutions. There is no obvious ciliostatic or ciliotoxicity present in short exposure or up to 24 hours.

5. Administration of Compositions Comprising Kappa-Carrageenan

A composition comprising kappa-carrageenan in an isotonic carrier solution was prepared by dissolving a commercially available powdered form of kappa-carrageenan in water to arrive at a final concentration of kappa-carrageenan about 0.12% wt/v. The amount of water may be selected from 50 ml, 100 ml or 200 ml. However, depending on the required use, other volumes may also be used. The powdered kappa-carrageenan may be added to water before or after the addition of the components required to achieve the isotonic carrier solution.

Although any isotonic carrier solution may be used in combination with the kappa-carrageenan, the best results are achieved with an isotonic solution comprising NaCl and KCl. For example, the carrier solution may be made from the FLO Sinus Care or FLO CRS. The carrier solution is made up in accordance with the manufacturer's instructions.

The subject to be treated with the above composition may be standing or seated during treatment. Preferably, the subject is located over a sink or bowl to ensure that the expelled carrier solution is contained after delivery to the nasal passages. The solution is applied to the nostril by a positive pressure irrigation device which is operated by simply squeezing the bottle until about 100 mL of the delivery solution has been expelled via one nostril into the nasal and paranasal sinus cavities and exits from the opposite nostril. This procedure is then repeated into the opposite nostril. To aid in delivery of the solution to the nasal sinuses, the subject may place their head down, in a nose to the ground position for irrigation of the nasal and sinus passages.

When used in children, a volume of about 50 ml per nostril should be sufficient to simultaneously cleanse and treat the mucous membranes. In adults, a volume of between 70-90 ml is generally sufficient to cleanse and treat the mucous membranes.

An example of the bottle for use in a positive pressure irrigation device is shown in FIG. 11. The bottle is designed to ensure delivery of the solution to the nasal and sinus passages. The bottle of FIG. 1 has a wide neck which permits the complete disassembly of the bottle components which can be rinsed and thoroughly dried after use. This significantly restricts the overgrowth of pathogenic bacteria and the subsequent re-infestation of the nasal passages, including the paranasal sinuses.

The composition described herein may be used on an ongoing basis, especially when used to treat Chronic Rhinosinusitis which is a life-long affliction. Thus the treatment may be indicated once daily or twice daily at most. Alternatively, the use of the composition may be used as directed by a physician.

6. Effect of Carrageenan Compositions in CRS Patients Compared to Controls

The effect of nasal spray solutions containing carrageenan (Iota or Kappa) on Ciliary Beat Frequency (CBF), mucosal barrier function and on inflammatory responses of primary human nasal epithelial cells grown at Air-liquid interface and harvested from nasal polyps of CRS patients and from non-CRS controls was tested.

6.1 Human Primary Nasal Epithelial Cells

Ethics approval to collect cytological nasal brushings from Chronic Rhinosinusitis (CRS) patients and non-CRS controls was granted from The Queen Elizabeth Hospital Human Research Ethics Committee. Nasal brushings were collected from consenting participants. Exclusion criteria included active smoking, age less than 18 years and systemic diseases.

Human Nasal Epithelial Cells (HNECs) were harvested from sinus mucosa by gentle brushing in a method as described in Ramezanpour M, et al., Th17 cytokines disrupt the airway mucosal barrier in chronic rhinosinusitis. *Mediators of inflammation*; Volume 2016, (2016). Extracted cells from Chronic Rhinosinusitis with nasal polyps xylitol (CR-SwNP) and non-CRS patients were suspended in Bronchial Epithelial Growth Media (BEGM, CC-3170, Lonza, Walkersville, Md., USA), then washed in phosphate buffered saline (PBS) with centrifugation (1700 rpm for 5 minutes) and resuspended in Clonetics™ B-ALI™ growth medium (Lonza, Walkersville, Md., USA).

Cell samples were then depleted of macrophages in a 100 mm diameter culture plate coated with anti-CD68 (Dako, Glostrup, Denmark) for 20 minutes. Cell samples were removed from the culture plate and seeded on flasks coated with type I collagen (Thermo Scientific, Walthman, Mass., USA). HNECs were tested at passage two, and confirmed to be of epithelial lineage via reactivity to pan-Cytokeratin and CD45 antibodies (both Abcam, Cambridge, Mass., USA).

6.2 Air Liquid Interface Culture

HNECs were maintained at an Air Liquid Interface (ALI) medium, following the Lonza ALI culture method (Lonza, Walkersville, USA) as described in Ramezanpour M, et al., Th17 Cytokines Disrupt the Airway Mucosal Barrier in Chronic Rhinosinusitis. *Mediators of Inflammation*, Volume 2016 (2016). Cells were grown until 80% confluent then harvested for seeding onto collagen coated 6.5 mm permeable Transwells (BD Biosciences, San Jose, Calif., USA) at a density of $7 \times 10^4$ cells per well. Cell cultures were maintained with B-ALI™ growth medium for 3-4 days in a cell incubator at 37° C. with 5% CO2. In the airlift step, the apical media was removed and the basal media replaced with 500 µl B-ALI™ differentiation medium. The cultures were fed every alternate day by adding B-ALI complete differentiation medium to the basal chamber. HNECs at air liquid interface (HNEC-ALI) were maintained for a minimum of 14 days for development of tight junctions and 28 days for cilia generation.

6.3 Carrageenan Sinonasal Solution

Kappa and Iota carrageenan were dissolved in sterile MQ water (Millipore, Billerica, Mass.) to a concentration of 0.24% by heating for 2 hours at 80° C. as directed by Marinomed Biotechnologies GmbH. FLO Sinus Care and FLO CRS (ENT Technologies, Australia) were suspended in sterile MQ water at a two-fold concentration. Each of the solutions were filter sterilised and then mixed at a 1:1 ratio to achieve: 0.12% Kappa carrageenan in FLO Sinus Care, 0.12% Iota carrageenan in FLO Sinus Care, 0.12% Kappa carrageenan in FLO CRS, and 0.12% Iota carrageenan in FLO CRS. Solutions were then stored at room temperature and applied to the apical compartment of the cell culture for up to 24 hours.

6.4 Transepithelial Electrical Resistance (TEER)

Transepithelial Electrical Resistance (TEER) was measured using an EVOM2 epithelial voltohmmeter (World Precision Instruments, FL) and results were expressed in Ohm as the raw value, or as a relative change to the initial reading. TEER values were only taken from cultures showing >400 $\Omega/cm^2$ (equivalent to >1200 ohm in a 0.33 cm2 transwell membrane). 100 µl of B-ALI medium was added to the apical chamber of ALI cultures to form an electrical circuit across the cell monolayer and into the basal chamber. Cultures were maintained at 37° C. during the measurement period using a heating platform. The corresponding treatment or control (B-ALI medium for the negative control and 2% Triton x100 for the positive control) was added to the bottom chamber of each well, and TEER measurements were obtained at time 0 and 24 h.

6.5 Permeability Assay

The paracellular permeability of the HNEC-ALI cultures was assessed following 24 hours of carrageenan exposure. A 4 kDa fluorescein isothiocyanate (FITC) dextran (Sigma-Aldrich, Saint Louis) was added to the apical compartment to a concentration of 3 mg/ml, samples were then taken from the basolateral compartment after 2 hours. The amount of passaged dextran was measured by a Fluostar Optima 96 well fluorescence microplate reader (FLUOstar Optima, BMG Labtech, Ortenberg, Germany) using wavelengths 485 nm and 520 nm for excitation and emission respectively.

6.6 Cytotoxicity Assay

All treatments were applied to the HNEC-ALI cultures and incubated for 24 h. Lactate dehydrogenase (LDH) was measured using a Cytotoxicity Detection Kit (Roche, CA) to determine cell viability. Briefly, 50 ml of the media from each well was transferred to a new plate, and 50 ml of LDH reagent was added to the supernatant and incubated for 30 minutes in the dark at room temperature. The absorbance of prepared samples was recorded at 490 nm on a FLUOstar OPTIMA plate reader (BMG Labtech, Ortenberg, Germany), and relative viability was calculated relative to the LDH levels of negative controls (untreated cells).

6.7 Enzyme-Linked Immunosorbent Assay (ELISA)

Supernatant was collected from the basolateral compartment of treated HNEC-ALI cultures after 24 hours of exposure to the treatments. Total matrix metallopeptidase-2 (MMP-2) and Interleukin-6 (IL-6) protein levels were determined with an MMP-2 (Invitrogen, CA, USA) and IL-6 ELISA kit (BD Biosciences, New Jersey), according to the manufacturer's instructions. All measurements were performed in duplicate. The tissue sample concentration was calculated from a standard curve and corrected for protein concentration.

6.8 Immunofluorescence Microscopy

Samples were fixed in formalin in phosphate-buffered saline (PBS) for 10 min, washed with PBS, permeabilised with 0.1% Triton X-100 in PBS on ice for 15 minutes, followed by blocking with serum free blocker (SFB; Dako, Glostrup, Denmark) for 60 minutes at room temperature. Mouse monoclonal anti-human ZO-1 antibodies (Invitrogen, Carlsbad, Calif., USA), diluted to 5 µg/ml in TBST-10% SFB was added overnight at 4° C. Excess primary antibody was removed, and 2 µg/ml anti-mouse Alexa-Fluor 488 conjugated secondary antibody (Jackson ImmunoResearch Labs Inc., West Grove, Pa., USA) was added and incubated for 1 hour at room temperature. The membranes were rinsed in PBS and 200 ng/ml of 4',6-diamidino-2-phenylindole (DAPI; Sigma, Aldrich) was added to resolve nuclei. Membranes were transferred to a glass slide and a drop of anti-fade mounting medium (Dako, Glostrup, Denmark) was added before cover-slipping. Samples were visualized by using an LSM700 confocal scanning laser microscope (Zeiss Microscopy, Germany).

6.9 Cilia Function and Structure

Ciliary beat frequency (CBF) of HNEC-ALI cultures was assessed using a 20× objective, and ×1.5 magnification on an inverted microscope (Olympus IX70, Tokyo). Video was recorded using a Model Basler acA645-100 µm USB3 camera (Basler AG, Ahrensburg, Germany) at 100 frames per second at a resolution of 640×480 pixels. The recorded video samples were analysed using the Sisson-Ammons Video Analysis (SAVA) system. All measurements were taken at room temperature. A baseline CBF was taken prior to addition of the experimental conditions. Initially HNEC-ALI cultures were washed with 100 µl of PBS then 40 µl of PBS was added to the apical compartment. Baseline measurements were taken from two separate regions from each culture. The apical PBS was removed and either the control media, vehicle only control or carrageenan containing solution was added. Sequential readings were taken every 5 minutes for the first 20 minutes to assess for any early stimulation/slowing of the CBF. Readings were also taken at 6 and 24 hours. Results are expressed as the mean CBF (Hz) and also as a percentile change when compared to baseline.

6.10 Statistical Analysis

Data is presented as the mean±SEM. The TEER experiment was performed using three replicates from CRS and non-CRS patients with values normalised against the mean value from the patient at time 0. The TEER statistical analysis was carried out using t-tests and all other analysis was performed using ANOVA, followed by Tukey's HSD post hoc test using SPSS (version 22).

Results 6.11 Results: Lactate Dehydrogenase Assay

Cell viability was assessed by measuring LDH release from HNEC-ALI cultures. A 24 h exposure of Kappa and Iota carrageenan in FLO CRS or FLO Sinus Care showed no significant increase in LDH release with any of the treatments in CRS patients (FIG. 12A) and non-CRS controls (FIG. 12B) ($P>0.05$).

Figure 12A:
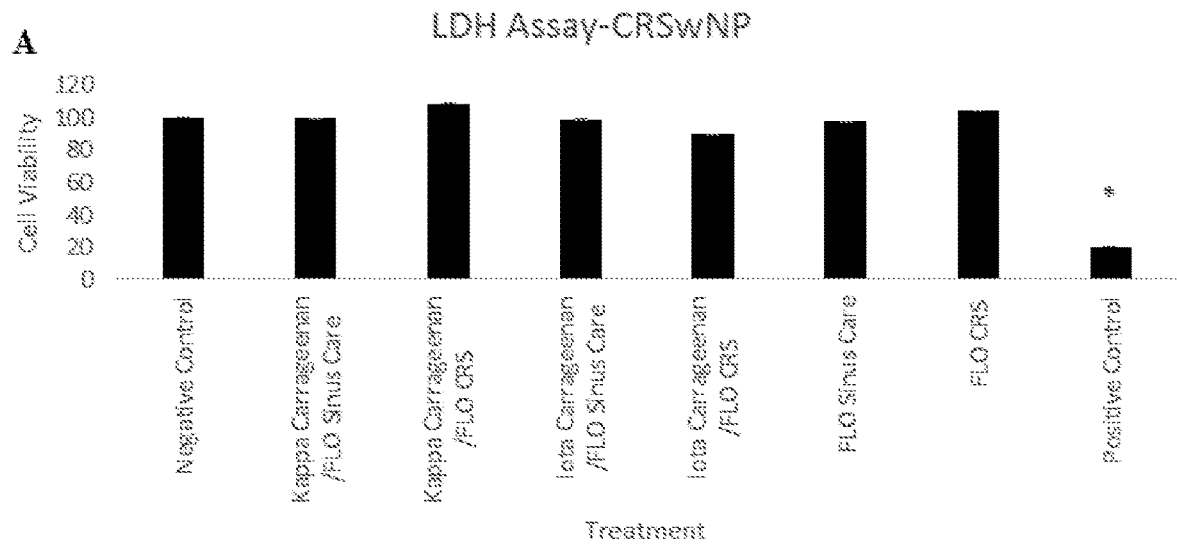
FIG. 12A is a graph showing lactate dehydrogenase release from HNEC-ALI cultures from CRS patients after a 24 hour exposure of Kappa or Iota carrageenan in FLO Sinus Care or FLO CRS solution. Expressed as cell viability ($P>0.05$)
Figure 12B:
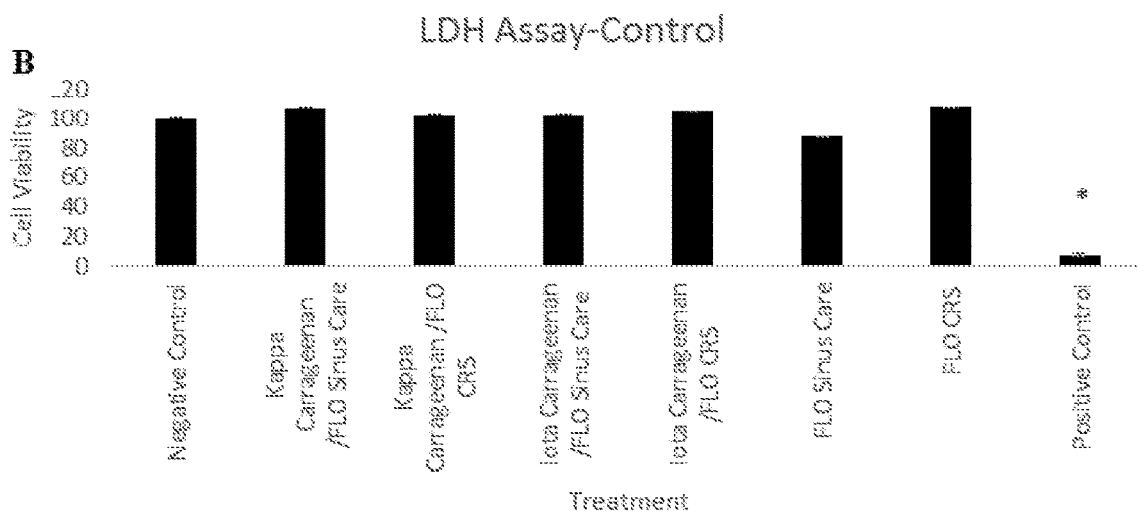
FIG. 12B is a graph showing lactate dehydrogenase release from HNEC-ALI cultures from non-CRS patients after a 24 hour exposure of Kappa or Iota carrageenan in FLO Sinus Care or FLO CRS solution. Expressed as cell viability ($P>0.05$)

Referring to FIGS. 12A and 12B, the graphs show the viability relative to no treatment control cells as determined by the LDH assay, 24 h after application of Kappa carrageenan/FLO Sinus Care, Kappa carrageenan/FLO CRS, Iota carrageenan/FLO Sinus Care, Iota carrageenan/FLO CRS, FLO Sinus Care, FLO CRS negative control (medium) and positive control (0.5% Triton X-100) in HNEC monolayers from CRS patients (FIG. 12A) and non-CRS control patients (FIG. 12B). Cell viability was calculated relative to the untreated cells as negative control. The values are shown as means±SEM, n=3. ANOVA, followed by Tukey HSD post hoc test. *=$p<0.05$.

6.12 Results: Matrix Metallopeptidase-2 ELISA

Application of Kappa carrageenan/FLO Sinus Care, Kappa carrageenan/FLO CRS, Iota carrageenan/FLO Sinus Care, Iota carrageenan/FLO CRS, FLO Sinus Care and FLO CRS did not alter the secretion of MMP-2 in the supernatant of HNECs after 24 hours in CRS patients and non-CRS control patients.

Figure 13A:
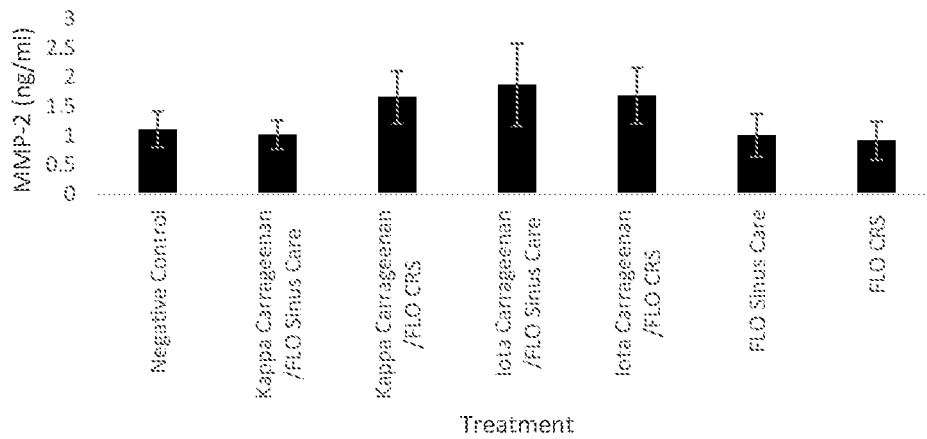
FIG. 13A is a graph showing matrix metallopeptidase-2 secretion in the supernatant of HNECs from CRS patients after a 24 hour exposure to carrageenan in FLO Sinus Care or FLO CRS solution. The values are shown as means±SEM for n=3, ANOVA, followed by Tukey HSD post hoc test
Figure 13B:
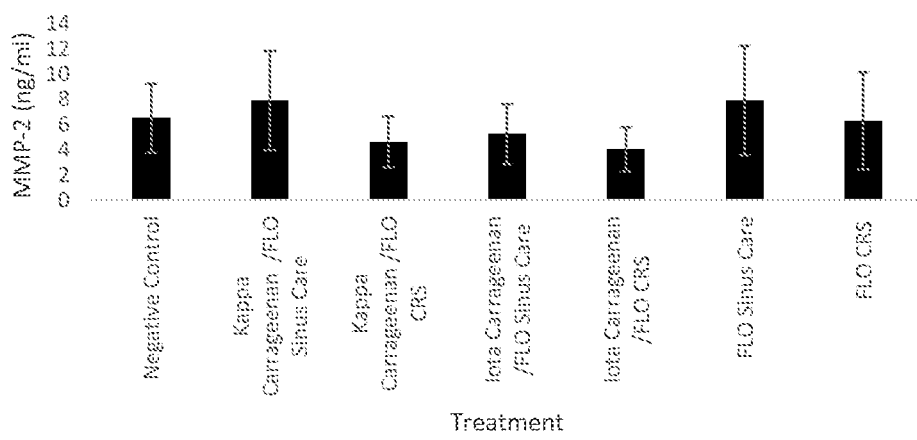
FIG. 13B is a graph showing matrix metallopeptidase-2 secretion in the supernatant of HNECs from non-CRS patients after a 24 hour exposure to carrageenan in FLO Sinus Care or FLO CRS solution. The values are shown as means±SEM for n=3, ANOVA, followed by Tukey HSD post hoc test

Matrix metalloproteinase-2 (MMP2) secretion by HNECs exposed to 24 hours of Kappa carrageenan/FLO Sinus Care, Kappa carrageenan/FLO CRS, Iota carrageenan/FLO Sinus Care, Iota carrageenan/FLO CRS, FLO Sinus Care, FLO CRS and negative control (medium) in HNEC monolayers from CRS patients (FIG. 13A) and non-CRS control patients (FIG. 13B), is expressed as total MMP2 levels (ng/ml). The values are shown as means±SEM for n=3. ANOVA, followed by Tukey HSD post hoc test.

6.13 Results: Interleukin-6 ELISA

Application of Kappa carrageenan in Flo Sinus Care for 24 hours significantly reduced IL-6 protein concentrations in supernatants of HNEC monolayers derived from CRS patients ($p=0.037$).

Figure 14A:
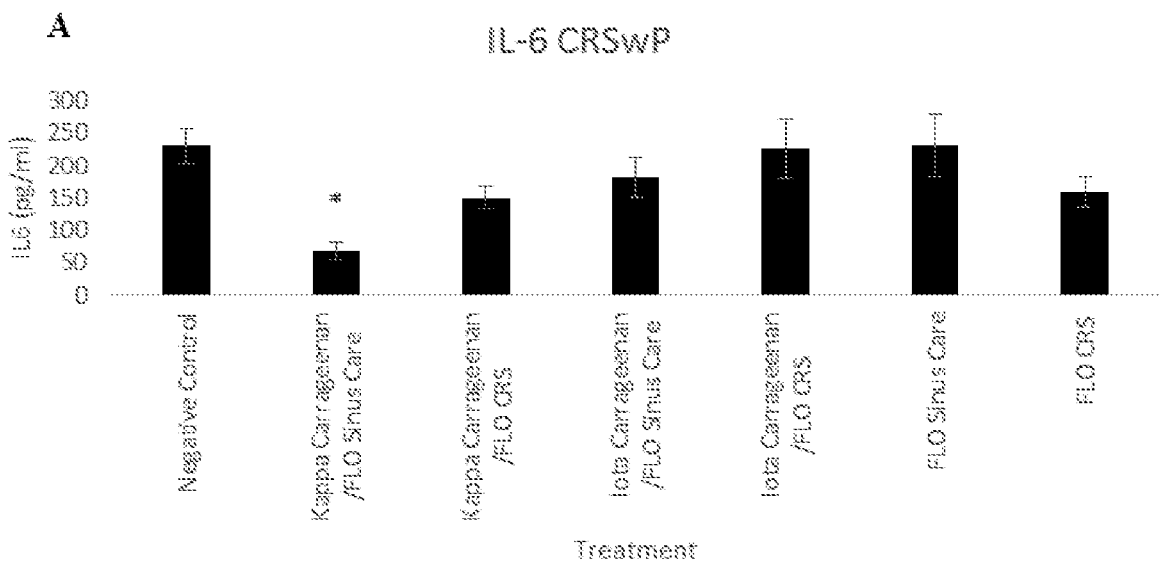
FIG. 14A is a graph showing Interleukin-6 levels in the supernatant of human nasal epithelial cells exposed to 24 hours of kappa carrageenan in FLO Sinus Care or FLO CRS solution from CRS patients. Expressed as total IL-6 (pg/ml); error bars represent standard deviation
Figure 14B:
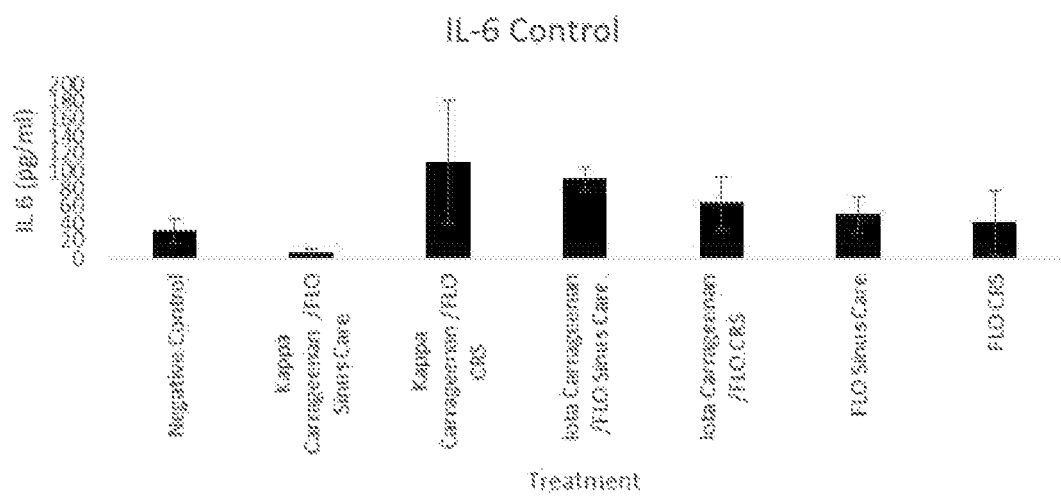
FIG. 14B is a graph showing Interleukin-6 levels in the supernatant of human nasal epithelial cells exposed to 24 hours of kappa carrageenan in FLO Sinus Care or FLO CRS solution from non-CRS patients. Expressed as total IL-6 (pg/ml); error bars represent standard deviation

Interleukin-6 protein levels in the supernatant of HNECs exposed to 24 hours of Kappa carrageenan/FLO Sinus Care, Kappa carrageenan/FLO CRS, Iota carrageenan/FLO Sinus Care, Iota carrageenan/FLO CRS, FLO Sinus Care, FLO CRS and negative control (medium) in HNEC monolayers from CRS patients (FIG. 14A) and non-CRS control patients (FIG. 14B), expressed as total (pg/ml). The values are shown as means±SEM for n=3. ANOVA, followed by Tukey HSD post hoc test. *=$p<0.05$.

6.14 Results: Trans-Epithelial Electrical Resistance (TEER)

Carrageenan Kappa/FLO CRS and FLO CRS increased TEER of HNEC ALI cultures. HNEC-ALI cultures were established from 6 donors (3 CRSwNP and 3 controls). The effect of Kappa carrageenan/FLO Sinus Care, Kappa carrageenan/FLO CRS, Iota carrageenan/FLO Sinus Care, Iota carrageenan/FLO CRS, FLO Sinus Care, FLO CRS, negative control (medium) and positive control (0.5% Triton X-100) was examined by measuring the TEER across HNEC monolayers from CRSwNP patients and controls after 24 h. Kappa carrageenan/Flo CRS ($p=0.04$) and FLO CRS ($p=0.02$) significantly increased TEER after 24 h of incubation in CRS patients. Other treatments did not show any significant effect on TEER in CRS patients or controls (FIGS. 15A and 15B).

Figure 15A:
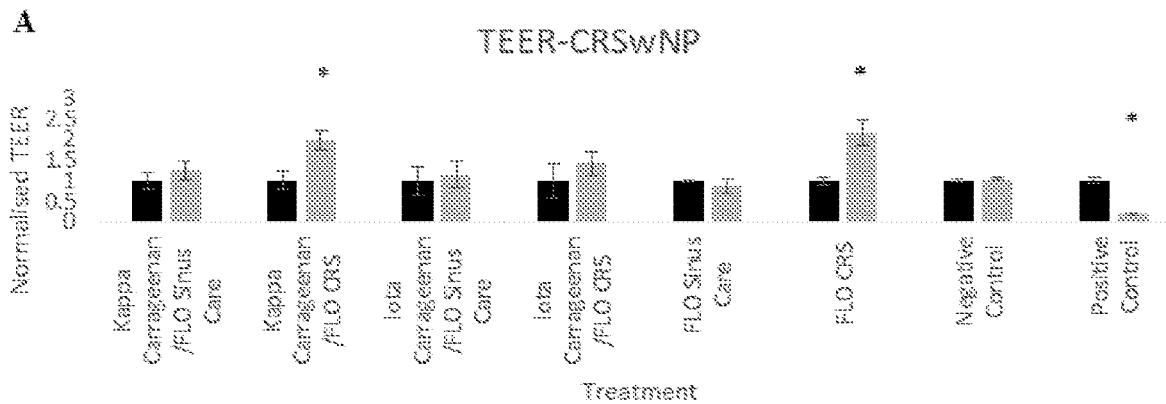
FIG. 15A is a graph showing the trans-epithelial electrical resistance (TEER) of human nasal epithelial cells exposed to 24 hours of Kappa or Iota carrageenan in either FLO Sinus Care or FLO CRS solution, measured in cell buffer from CRS patients
Figure 15B:
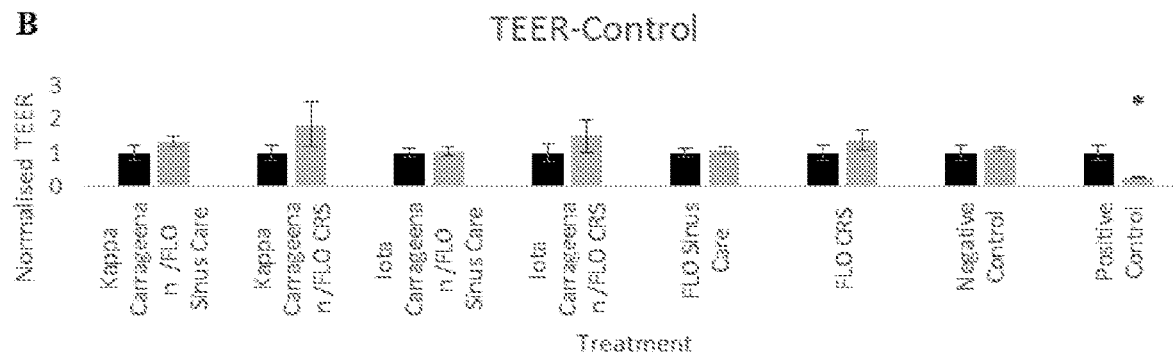
FIG. 15B is a graph showing the trans-epithelial electrical resistance (TEER) of human nasal epithelial cells exposed to 24 hours of Kappa or Iota carrageenan in either FLO Sinus Care or FLO CRS solution, measured in cell buffer from non-CRS patients

TEER values, normalised to the measurement prior to treatment (as shown in FIGS. 15A and 15B as black bars) and 24 hours after (grey bars) application of Kappa carrageenan/FLO Sinus Care, Kappa carrageenan/FLO CRS, Iota carrageenan/FLO Sinus Care, Iota carrageenan/FLO CRS, FLO Sinus Care, FLO CRS, negative control (medium) and positive control (0.5% Triton X-100) in HNEC monolayers from CRSwNP patients (A) and non-CRS control patients (B). The values are shown as means±SEM for n=3. *=$p<0.05$, using t-tests.

6.15 Results: Parcellular Permeability—Dextan Assay

Figure 16A:
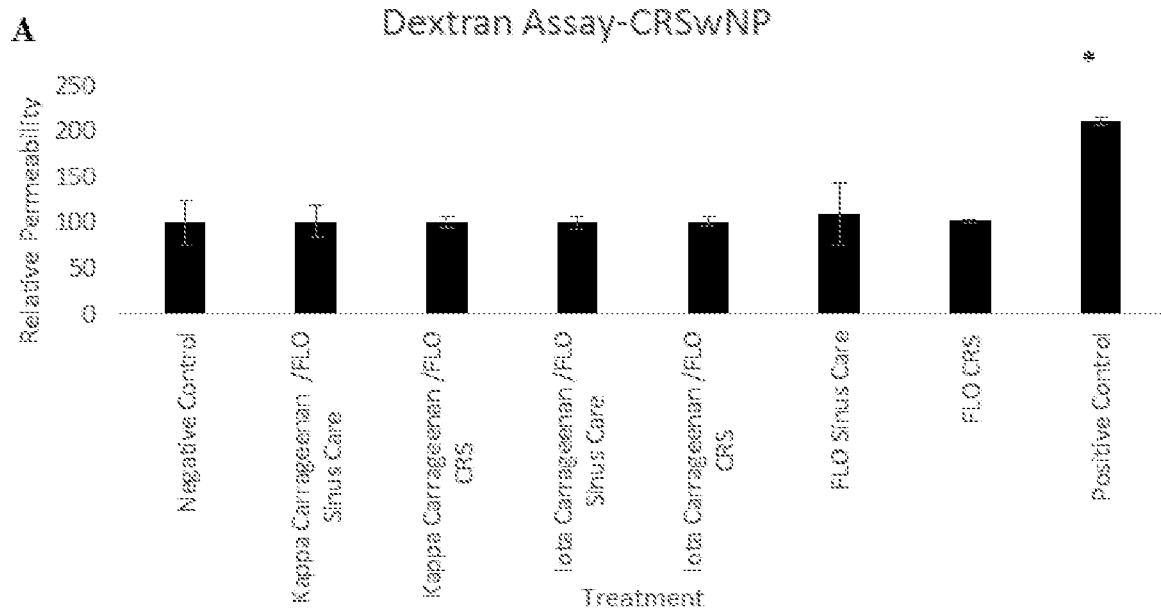
FIG. 16A is a graph showing the paracellular permeability of HNEC-ALI monolayers derived from CRS patients. The passage of FITC-Dextrans was measured 24 hours after application of Kappa carrageenan/FLO Sinus Care, Kappa carrageenan/FLO CRS, Iota carrageenan/FLO Sinus Care, Iota carrageenan/FLO CRS, FLO Sinus Care, FLO CRS, negative control (medium) and positive control (0.5% Triton X-100) in HNEC monolayers from CRSwNP patients. The values are shown as means±SEM for n=3. ANOVA, followed by Tukey HSD post hoc test. *=p<0.05

Kappa or Iota carrageenan in FLO Sinus Care or FLO CRS did not increase the paracellular permeability of HNEC-ALI cultures. Application of Kappa carrageenan/FLO Sinus Care, Kappa carrageenan/FLO CRS, Iota carrageenan/FLO Sinus Care, Iota carrageenan/FLO CRS, FLO Sinus Care and FLO CRS did not have a significant effect on the paracellular permeability in HNEC-ALI monolayers sourced from CRS patients and controls (FIGS. 16A and 16B) (P>0.05). The positive control (0.5% Triton X-100) (low permeability) and negative control (medium) (high permeability) demonstrated expected permeability values.

Figure 16B:
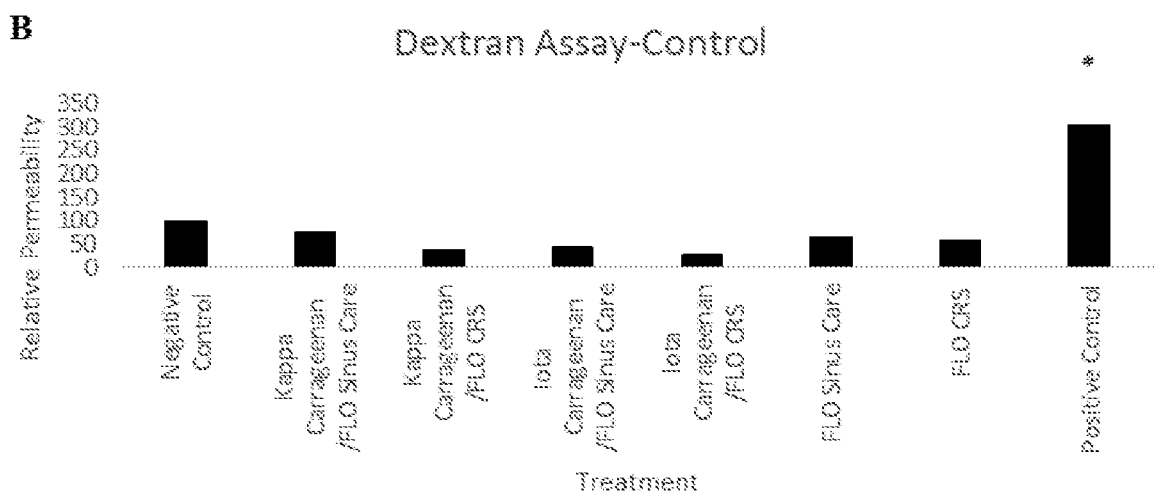
FIG. 16B is a graph showing the paracellular permeability of HNEC-ALI monolayers derived from CRS patients. The passage of FITC-Dextrans was measured 24 hours after application of Kappa carrageenan/FLO Sinus Care, Kappa carrageenan/FLO CRS, Iota carrageenan/FLO Sinus Care, Iota carrageenan/FLO CRS, FLO Sinus Care, FLO CRS, negative control (medium) and positive control (0.5% Triton X-100) in HNEC monolayers from non-CRS control patients. The values are shown as means±SEM for n=3. ANOVA, followed by Tukey HSD post hoc test. *=p<0.05

Passage of FITC-Dextrans measured 24 hours after application of Kappa carrageenan/FLO Sinus Care, Kappa carrageenan/FLO CRS, Iota carrageenan/FLO Sinus Care, Iota carrageenan/FLO CRS, FLO Sinus Care, FLO CRS, negative control (medium) and positive control (0.5% Triton X-100) in HNEC monolayers from CRSwNP patients (FIG. 16A) and non-CRS control patients is shown in FIG. 16B. The values are shown as means±SEM for n=3. ANOVA, followed by Tukey HSD post hoc test. *=p<0.05.

6.16 Results: Actin Cyctoskeleton Immunocytochemistry

Kappa or Iota carrageenan in FLO Sinus Care or FLO CRS did not affect the localisation of ZO-1 and F-actin in HNEC-ALI monolayers. The effect of Kappa carrageenan/FLO Sinus Care, Kappa carrageenan/FLO CRS, Iota carrageenan/FLO Sinus Care, Iota carrageenan/FLO CRS, FLO Sinus Care and FLO CRS on the localization of ZO-1 and F-actin was examined by using immunofluorescence and confocal laser scanning microscopy, 24 hours after application of the treatments. In untreated cells, ZO-1 or F-actin was located at the periphery of the apical side of the monolayer, as expected. Confocal imaging of Kappa and Iota carrageenan in either FLO Sinus Care or FLO CRS showed no alterations in the localization of ZO-1 or F-actin in CRS patients and non-CRS control patients.

Figure 17A:
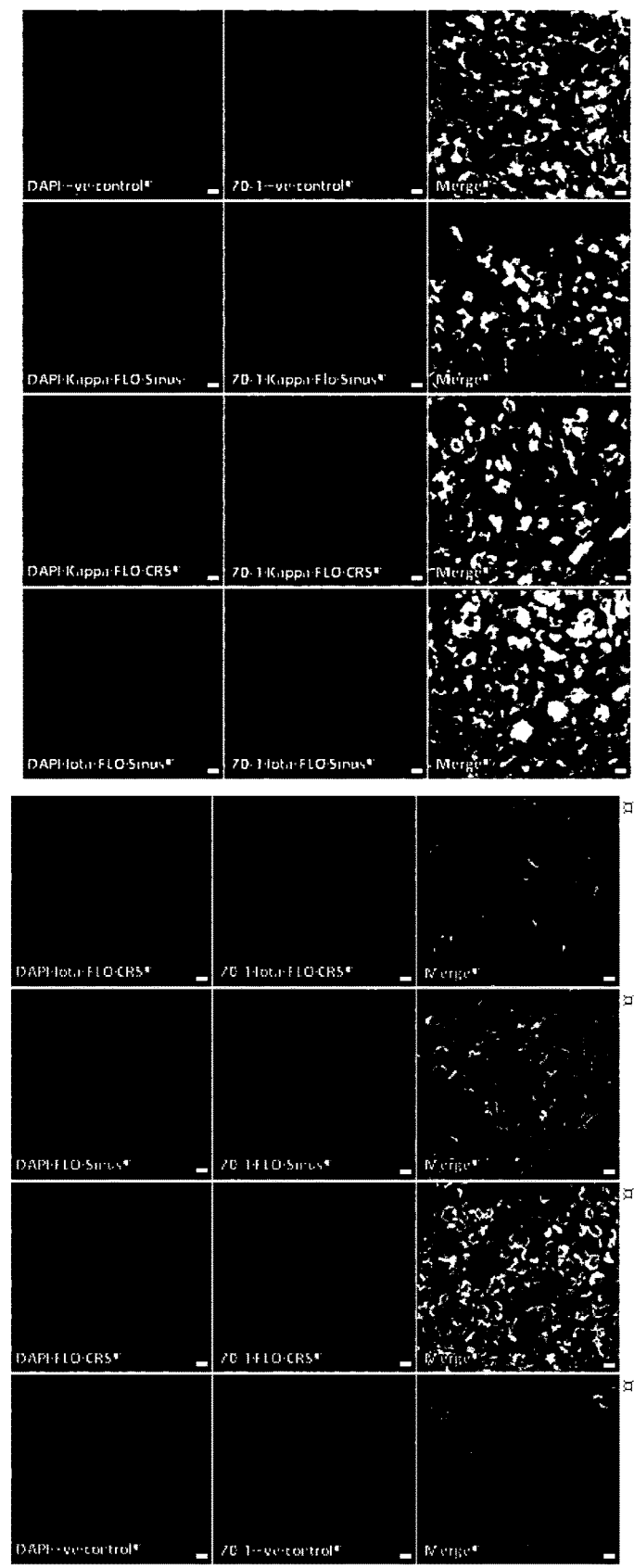
FIG. 17A shows the effect of Kappa Carrageenan/Flo Sinus Care, Kappa Carrageenan/Flo CRS, Iota Carrageenan/FLO Sinus Care, Iota Carrageenan/FLO CRS, FLO Sinus Care and FLO CRS, negative control (medium) and positive control (0.5% Triton X-100) on Zona Occludens-1 (ZO-1) immunolocalization of HNEC monolayers of CRS patients. DAPI was used to stain the nuclei (blue staining), white bar is 20 μm. 20× magnification, using confocal laser scanning microscopy
Figure 17B:
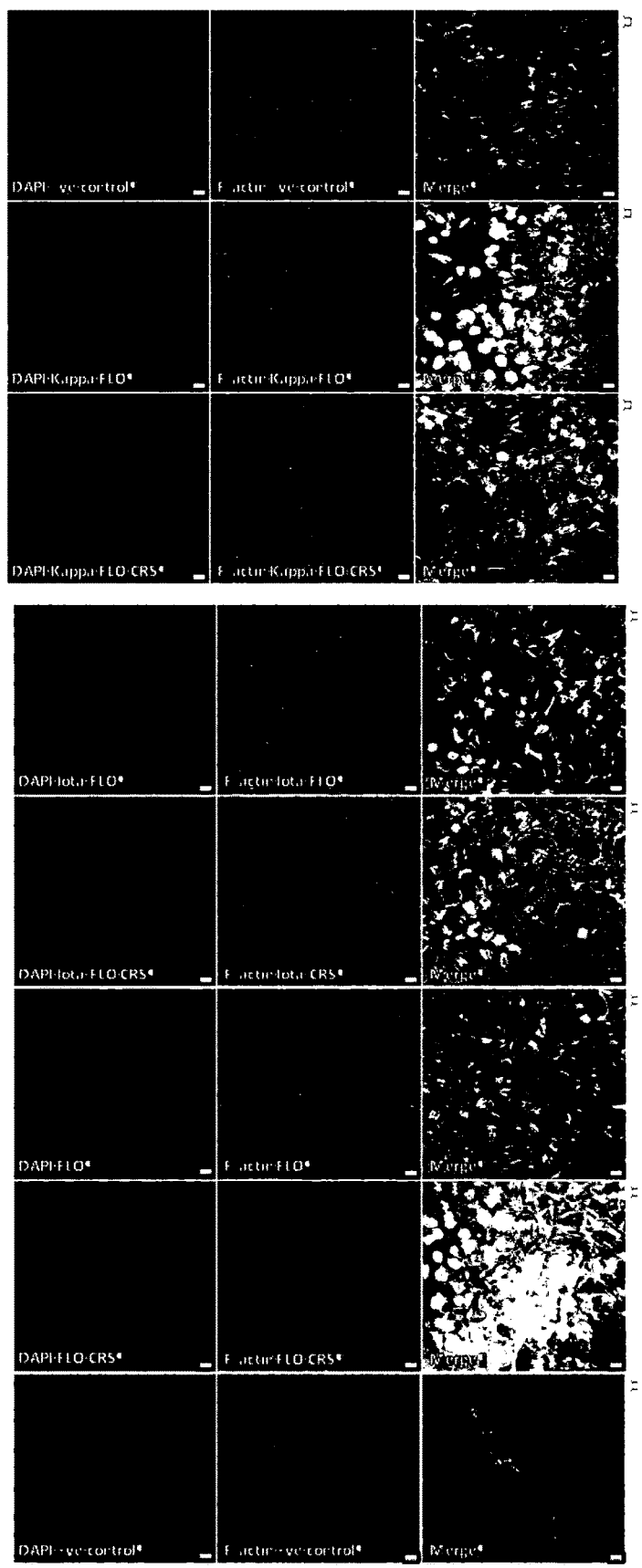
FIG. 17B shows the effect of Kappa Carrageenan/Flo Sinus Care, Kappa Carrageenan/Flo CRS, Iota Carrageenan/FLO Sinus Care, Iota Carrageenan/FLO CRS, FLO Sinus Care and FLO CRS, negative control (medium) and positive control (0.5% Triton X-100) on F-actin of CRS patients. DAPI was used to stain the nuclei (blue staining), white bar is 20 μm. 20× magnification, using confocal laser scanning microscopy

Immunolocalization of ZO-1 and F-actin in HNEC monolayers of CRS patients and controls were investigated. The effect of Kappa Carrageenan/Flo Sinus Care, Kappa Carrageenan/Flo CRS, Iota Carrageenan/FLO Sinus Care, Iota Carrageenan/FLO CRS, FLO Sinus Care and FLO CRS, negative control (medium) and positive control (0.5% Triton X-100) on Zona Occludens-1 (ZO-1) immunolocalization of HNEC monolayers of CRS patients (FIG. 17A) and F-actin CRS patients (FIG. 17B). DAPI was used to stain the nuclei (blue staining), white bar is 20 μm. 20× magnification, using confocal laser scanning microscopy.

6.17 Results: Cilia Beat Frequency

Kappa or Iota carrageenan in FLO Sinus Care or FLO CRS did not affect the cilia beat frequency after 24 hours in HNEC-ALI monolayers. Cilia beat frequency was assessed on different time point (0, 5 min, 10 min, 20 min, 6 h and 24 h) in HNEC-ALI cultures. A 24 h exposure of Kappa and Iota carrageenan in FLO CRS or FLO Sinus Care showed no significant difference in CBF with any of the treatments in CRS and non-CRS patients. Measurements represent the mean (Hz) over the time points: 5 minutes, 10 minutes, 20 minutes, 6 hours, and 24 hours. The values are shown as means±SEM for n=3 (FIG. 18).

6.18 Results: Treatment Effects on Cell Migration—Control Patients

Figure 19A:
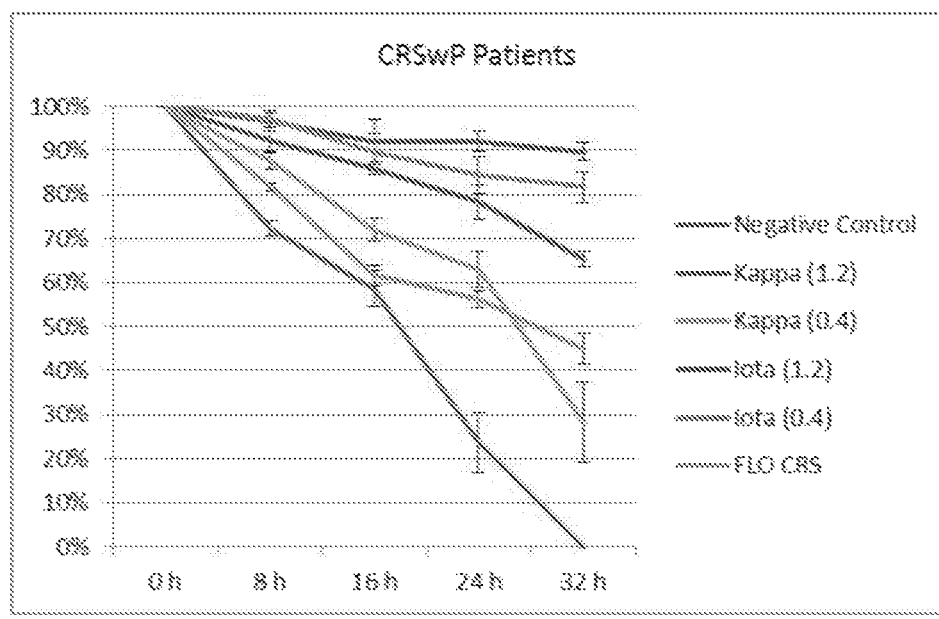
FIG. 19A is a graph showing the effect of treatment on cell migration. Wound healing migration assay was measured 24 hours after application of Kappa carrageenan/FLO CRS, Iota carrageenan/FLO CRS, FLO CRS and negative control (medium) in HNEC monolayers from CRSwNP patients The values are shown as means±SEM for n=3. ANOVA, followed by Tukey HSD post hoc test. *=p<0.05
Figure 19B:
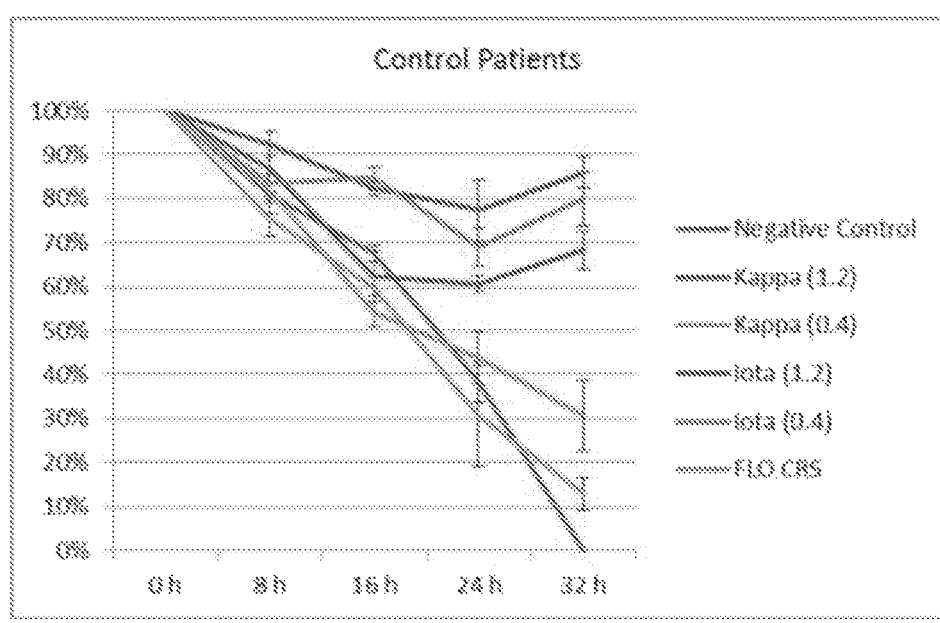
FIG. 19B is a graph showing the effect of treatment on cell migration. Wound healing migration assay was measured 24 hours after application of Kappa carrageenan/FLO CRS, Iota carrageenan/FLO CRS, FLO CRS and negative control (medium) in HNEC monolayers from and non-CRS control patients. The values are shown as means±SEM for n=3. ANOVA, followed by Tukey HSD post hoc test. *=p<0.05.

The effect of treatment on cell migration for control patients was investigated. Compared to the negative control, there was no significant difference in the rate of migration with treatments Kappa (0.4 mg/ml)+FLO CRS (p=0.461) and FLO CRS (p=0.095). The rate of migration was slower than the negative control with treatments Kappa (1.2 mg/ml)+FLO CRS (p=0.015), Iota (1.2 mg/ml)+FLO CRS (p=0.001), and Iota (0.4 mg/ml)+FLO CRS (p=0.003). Results are shown in FIG. 19A and FIG. 19B. Data is mean±SD with rates of migration compared by linear regression analysis. Differences considered significant when p 0.05.

Wound healing migration assay was measured 24 hours after application of Kappa carrageenan/FLO CRS, Iota carrageenan/FLO CRS, FLO CRS and negative control (medium) in HNEC monolayers from CRSwNP patients (FIG. 19A) and non-CRS control patients (FIG. 19B). The values are shown as means±SEM for n=3. ANOVA, followed by Tukey HSD post hoc test. *=p<0.05.

6.19 Results: Inflammatory Response

Kappa or Iota carrageenan in FLO Sinus Care or FLO CRS did not did not inhibit pro-inflammatory response of IL-6 in HNEC/ALI in CRS patients. Previous studies have shown that Poly (I: C) LMW consistently induces inflammatory cytokines secretion, including IL-6 and TNF-α, by HNEC/ALI monolayers. To determine the potential of carrageenan Iota and Kappa to dampen a pro-inflammatory response, both carrageenans in FLO CRS and FLO Sinus Care were applied to HNEC/ALI monolayers derived from CRS patients and Non-CRS controls in the absence or presence of Poly(I:C) LMW (10 pg/ml). Budesonide used as anti-inflammatory standard of care control. The analysis of IL-6 cytokine revealed that the following treatments with carrageenan Kappa/FLO Sinus Care Kappa/FLO Sinus Care, Carrageenan Kappa/FLO CRS, Carrageenan Iota/FLO Sinus Care, Carrageenan Iota/FLO CRS, FLO Sinus Care and FLO CRS did not suppress the pro-inflammatory response in CRS and non-CRS patients.

Figure 20A:
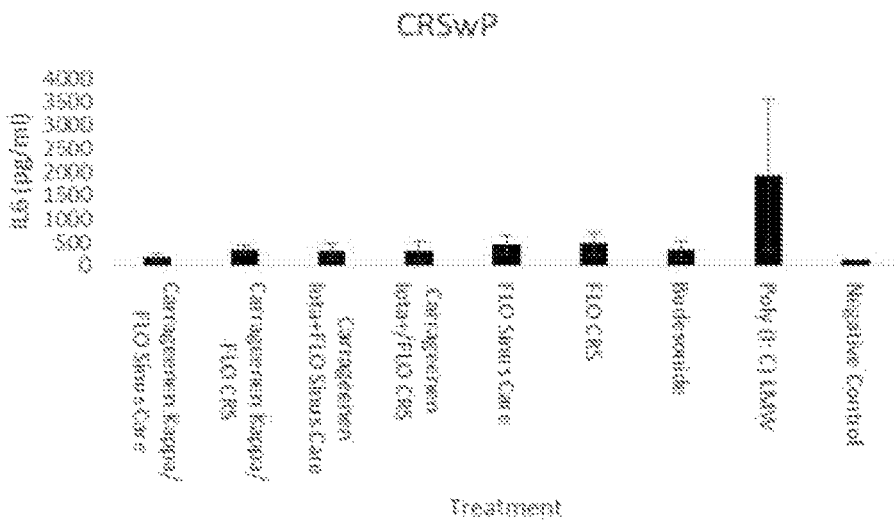
FIG. 20A is a graph showing the effect of Kappa or Iota carrageenan delivered in FLO CRS and FLO Sinus Care on dampening a pro-inflammatory response. The effect of Carrageenan Kappa/FLO Sinus Care, Carrageenan Kappa/FLO CRS, Carrageenan Iota/FLO Sinus Care, Carrageenan Iota/FLO CRS, FLO Sinus Care and FLO CRS on HNEC/ALI while stimulated with Poly (I:C)LMW in CRS patients. Budesonide was used as anti-inflammatory standard of care control. Negative control is untreated cell (medium). Data shown as a mean±SD (n=3)
Figure 20B:
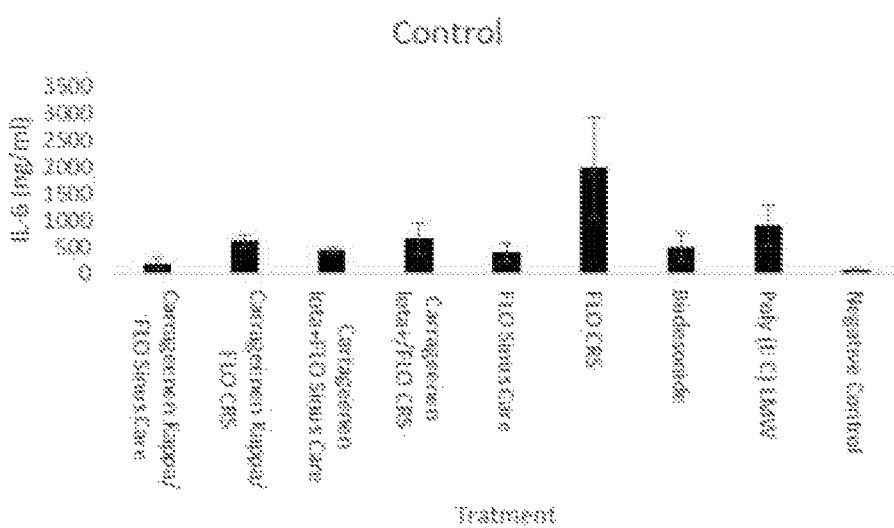
FIG. 20B is a graph showing the effect of Kappa or Iota carrageenan delivered in FLO CRS and FLO Sinus Care on dampening a pro-inflammatory response. The effect of Carrageenan Kappa/FLO Sinus Care, Carrageenan Kappa/FLO CRS, Carrageenan Iota/FLO Sinus Care, Carrageenan Iota/FLO CRS, FLO Sinus Care and FLO CRS on HNEC/ALI while stimulated with Poly (I:C)LMW in non-CRS patients. Budesonide was used as anti-inflammatory standard of care control. Negative control is untreated cell (medium). Data shown as a mean±SD (n=3)

The effect of Kappa or Iota carrageenan delivered in FLO CRS and FLO Sinus Care on dampening a pro-inflammatory response was investigated and the results are shown in FIGS. 20A and 20B. The effect of Carrageenan Kappa/FLO Sinus Care, Carrageenan Kappa/FLO CRS, Carrageenan Iota/FLO Sinus Care, Carrageenan Iota/FLO CRS, FLO Sinus Care and FLO CRS on HNEC/ALI while stimulated with Poly (I:C)LMW in CRS (FIG. 20A) and non-CRS (FIG. 20B) patients. Budesonide used as anti-inflammatory standard of care control. Negative control is untreated cell (medium). Data shown as a mean±SD (n=3).

Discussion

Defective epithelial tight junction (TJ) barrier function has been shown to be a pathogenic factor in the development of inflammatory diseases of the upper airways. In this present study discussed above, the effect of Kappa or Iota carrageenan was assessed in either FLO Sinus Care or FLO CRS on the mucociliary function and barrier structure and function of primary human nasal epithelial cells harvested from CRS patients and non-CRS (control) patients.

The study indicated that these treatments were not toxic and did not have detrimental effects on epithelial barrier function. Rather, application of FLO CRS (isotonic solution), with or without Kappa carrageenan significantly enhanced the TEER of human nasal epithelial cell monolayers derived from CRS patients after 24 hours. Changes in TEER were not associated with changes in paracellular permeability compared to the negative controls, evidenced by equivalent paracellular passage of fluorescently labelled beads upon application of the different treatments. These findings indicate that FLO CRS with/without Kappa carrageenan could discretely strengthen mucosal barrier function mainly in inflammatory conditions such as in CRS patients. It is well known that the ionic strength of solutions directly influence TEER readings and it could also be that the increased TEER readings could at least in part be explained by differences in ionic composition of these solutions compared to the negative control solution. Regardless, the notion that the observed effect is donor-dependent, indicates differences in the physiology of CRS and control HNECs, even after multiple in vitro cell divisions took place.

Interleukin-6 (IL-6) is an important pro-inflammatory cytokine and plays a significant role in chronic allergic airway inflammation. IL-6 causes acute phase responses and triggers intracellular signalling cascades which regulate inflammation. Specific carrageenan variants are known to induce inflammation, protecting the organism from infections. However, the degree of protection depends on the structure of the polysaccharides which differ between the different types of carrageenans. Indeed, lambda carrageen can effectively induce IL-6 secretion while kappa carrageenan has minimal effects on IL-6 induction. The molecular weight of the carrageenan (determined by the number of ester sulphate groups) plays a crucial role in the immune-stimulating properties of those molecules. The European Commission advised a molecular weight greater than 50 kDa for carrageenan used as food additive to avoid any safety risk.

Kappa and Iota carrageenan used in this study have a molecular weight of around 200 and 500 kDa respectively. The results indicate that IL-6 protein levels in the supernatants of HNEC-ALI monolayers from CRS patients were decreased in the presence of Kappa carrageenan diluted in FLO Sinus Care. These results indicate that Kappa carrageenan when diluted in FLO Sinus Care may have anti-inflammatory properties. It is unclear whether the decreased IL-6 protein levels in the supernatants is due to a decreased production and secretion of IL-6 by the HNEC-ALI cells or, alternatively, Kappa Carrageenan in FLO Sinus Care could partially complex the IL-6 protein within the supernatants. Nevertheless, Kappa carrageenan has been shown in this study to have anti-inflammatory properties.

It will also be interesting to determine whether the observed effect is specific to IL-6 or whether other cytokines, such as FGF-2, Fractalkine, GRO, G-CSF, IL-8, IL-1a, IP-10, IL-10, and IFN-α2, could also be affected by the presence of Kappa carrageenan in FLO Sinus Care.

In light of the IL-6 results, the affect of Kappa carrageenan on the inhibition of a pro-inflammatory response in HNEC/ALI culture from CRS and non-CRS patients was investigated. The HNEC/ALI culture stimulated with Poly (I: C) LMW in the presence of Kappa carrageenan did not dampen the pro-inflammatory response of IL-6. The other polymer Iota carrageenan in either FLO Sinus Care or FLO CRS did not down regulate the production of IL-6.

Matrix Metalloproteinase-2 (MMP-2) plays a major role in tissue repair and remodelling within the respiratory epithelium. Elevated levels of MMP-2 have previously been found in nasal polyposis. In this present study, MMP-2 was found to be present at low levels in supernatants of HNEC-ALI monolayers derived from CRS and non-CRS patients, and Kappa or Iota carrageenan solutions did not affect MMP-2 protein levels.

The actin cytoskeleton is important in maintaining cell polarity, vesicle transport, and is intimately associated with the cell junction complexes including tight junctions and adherens junctions and desmosomes. Tight junctions serve as a fence which differentiates the plasma membrane into apical and basolateral domains and also serve as a gate which controls the paracellular passage of ions and solutes between adjacent cells. In tight junction formation, ZO-1 is an essential protein between transmembrane proteins occludin, claudin and Junction Adhesion Molecule (JAM) and cytoplasmic components which form a belt between Adherens and Tight junctions. The present findings show that Kappa and Iota carrageenan in either FLO Sinus Care or FLO CRS did not affect the localisation of ZO-1 or actin, indicating that they did not compromise the mucosal barrier structure.

In summary, the results of this study indicate that Kappa or Iota carrageenan in either FLO Sinus Care or FLO CRS were not cytotoxic to HNEC-ALI monolayers, did not induce a pro-inflammatory response and did not compromise mucosal barrier structure or function. FLO CRS with and without Kappa Carrageenan increased TEER while secreted IL-6 levels were decreased in the presence of Kappa Carrageenan in FLO Sinus Care. Together this data indicates that Iota and Kappa Carrageenans diluted in FLO CRS and FLO Sinus Care could have beneficial properties on mucosal barrier structure and function and could reduce inflammation when applied topically.

The invention claimed is:

1. A composition comprising kappa-carrageenan in an amount of about 0.01% to about 15% wt/v and a carrier solution, wherein the carrier solution is an isotonic solution having an ionic strength of less than normal saline, wherein the carrier solution comprises NaCl and KCl and wherein the composition is a solution.

2. The composition according to claim 1, further comprising a second active agent, wherein the second active agent is an anti-viral agent, antibiotic, antifungal agent, anti-inflammatory agent or antioxidant.

3. The composition according to claim 1, wherein the amount of kappa-carrageenan is about 0.12% wt/v.

4. The composition according to claim 1, wherein the volume of the carrier solution is about 50 ml to about 350 ml.

5. The composition according to claim 1, wherein the carrier solution further comprises one or more of calcium lactate pentahydrate, sodium bicarbonate, glucose, xylitol, erythritol, or diluent.

6. The composition of claim 1, wherein the isotonic carrier solution further comprises xylitol.

* * * * *